US009863806B2

(12) United States Patent
Tanabe

(10) Patent No.: US 9,863,806 B2
(45) Date of Patent: *Jan. 9, 2018

(54) OPTICAL ANALYSIS METHOD AND OPTICAL ANALYSIS DEVICE USING THE DETECTION OF LIGHT FROM A SINGLE LIGHT-EMITTING PARTICLE

(71) Applicant: OLYMPUS CORPORATION, Tokyo (JP)

(72) Inventor: Tetsuya Tanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/946,091

(22) Filed: Jul. 19, 2013

(65) Prior Publication Data

US 2013/0302906 A1 Nov. 14, 2013

Related U.S. Application Data

(63) Continuation of application No. PCT/JP2012/051175, filed on Jan. 20, 2012.

(30) Foreign Application Priority Data

Jan. 20, 2011 (JP) .................................. 2011-009496

(51) Int. Cl.
*G01J 1/42* (2006.01)
*G01N 21/64* (2006.01)
(Continued)

(52) U.S. Cl.
CPC ............ *G01J 1/42* (2013.01); *G01N 21/6452* (2013.01); *G02B 21/0076* (2013.01); *G02B 21/16* (2013.01)

(58) Field of Classification Search
None
See application file for complete search history.

(56) References Cited

U.S. PATENT DOCUMENTS 4,251,733 A 2/1981 Hirleman, Jr.
4,885,473 A 12/1989 Shofner et al.
(Continued)

FOREIGN PATENT DOCUMENTS

CN 101946180 A 1/2011
EP 1 906 172 A1 4/2008
(Continued)

OTHER PUBLICATIONS

M. Kinjo, "Single molecule detection by fluorescence correlation spectroscopy", Proteins, Nucleic Acids and Enzymes, 1999, vol. 44, No. 9, pp. 1431-1438.
(Continued)

*Primary Examiner* — Xiaoyun R Xu
(74) *Attorney, Agent, or Firm* — Westerman, Hattori, Daniels & Adrian, LLP

(57) ABSTRACT

In the scanning molecule counting method using the light measurement with a confocal microscope or a multiphoton microscope, a measuring time is optimized with suppressing the scattering in a result small irrespective of light-emitting particle concentrations. In the inventive technique of detecting and analyzing the light from an light-emitting particle, there are repeated processes of detecting the light intensity from a light detection region with moving the position of the light detection region of an optical system in a sample solution by changing the optical path of the optical system of the microscope, and detecting the signals of the light of light-emitting particles individually, and based on the time taken for the number of the signals from the light-emitting
(Continued)

particles to reach a predetermined number, the light-emitting particle concentration in the sample solution is determined.

8 Claims, 11 Drawing Sheets

(51) Int. Cl.
  *G02B 21/00* (2006.01)
  *G02B 21/16* (2006.01)

(56) References Cited

U.S. PATENT DOCUMENTS

| | | | |
|---|---|---|---|
| 4,979,824 A | 12/1990 | Mathies et al. | |
| 5,319,575 A * | 6/1994 | Lilienfeld | 702/26 |
| 5,866,336 A | 2/1999 | Nazarenko et al. | |
| 5,900,933 A | 5/1999 | Schwartz et al. | |
| 6,280,960 B1 | 8/2001 | Carr | |
| 6,376,843 B1 | 4/2002 | Palo | |
| 6,388,746 B1 | 5/2002 | Eriksson et al. | |
| 6,388,788 B1 | 5/2002 | Harris et al. | |
| 6,400,487 B1 | 6/2002 | Harris et al. | |
| 6,403,338 B1 | 6/2002 | Knapp et al. | |
| 6,449,042 B1 | 9/2002 | Hamann | |
| 6,563,583 B2 | 5/2003 | Ortyn et al. | |
| 6,710,871 B1 | 3/2004 | Goix | |
| 6,782,297 B2 * | 8/2004 | Tabor | 700/55 |
| 6,856,391 B2 | 2/2005 | Garab et al. | |
| 6,927,401 B1 | 8/2005 | Palo | |
| 8,284,484 B2 | 10/2012 | Hoult et al. | |
| 9,068,944 B2 | 6/2015 | Tanabe | |
| 2001/0035954 A1 | 11/2001 | Rahn et al. | |
| 2002/0008211 A1 | 1/2002 | Kask | |
| 2002/0036775 A1 | 3/2002 | Wolleschensky et al. | |
| 2003/0036855 A1 | 2/2003 | Harris et al. | |
| 2003/0218746 A1 | 11/2003 | Sampas | |
| 2004/0022684 A1 | 2/2004 | Heinze et al. | |
| 2004/0036870 A1 | 2/2004 | Goix | |
| 2004/0051051 A1 | 3/2004 | Kato et al. | |
| 2004/0150880 A1 | 8/2004 | Nakata et al. | |
| 2005/0260660 A1 | 11/2005 | van Dongen et al. | |
| 2006/0078998 A1 | 4/2006 | Puskas et al. | |
| 2006/0158721 A1 | 7/2006 | Nakata et al. | |
| 2006/0256338 A1 | 11/2006 | Gratton et al. | |
| 2007/0250274 A1 | 10/2007 | Volkov et al. | |
| 2008/0052009 A1 | 2/2008 | Chiu et al. | |
| 2008/0156999 A1 | 7/2008 | Nishiwaki et al. | |
| 2008/0158561 A1 | 7/2008 | Vacca et al. | |
| 2009/0159812 A1 * | 6/2009 | Livingston | 250/428 |
| 2010/0033718 A1 | 2/2010 | Tanaami | |
| 2010/0177190 A1 | 7/2010 | Chiang et al. | |
| 2010/0202043 A1 | 8/2010 | Ujike | |
| 2010/0301231 A1 | 12/2010 | Yamaguchi | |
| 2011/0001969 A1 | 1/2011 | Ishii et al. | |
| 2011/0192595 A1 | 8/2011 | Ronaes et al. | |
| 2014/0099630 A1 | 4/2014 | Nakata | |
| 2014/0134608 A1 | 5/2014 | Hanashi et al. | |
| 2014/0162268 A1 | 6/2014 | Tanabe et al. | |

FOREIGN PATENT DOCUMENTS

| | | |
|---|---|---|
| EP | 2 752 655 A | 7/2014 |
| EP | 2 840 380 A1 | 2/2015 |
| JP | 63-225145 A | 9/1988 |
| JP | 04-337446 A | 11/1992 |
| JP | 2002-507762 A | 3/2002 |
| JP | 2002-543414 A | 12/2002 |
| JP | 2004-506192 A | 2/2004 |
| JP | 2005-098876 A | 4/2005 |
| JP | 2005-099662 A | 4/2005 |
| JP | 2007-20565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-190730 A | 9/2010 |
| JP | 2011-2415 A | 1/2011 |
| WO | 98/16814 A1 | 4/1998 |
| WO | 99/47963 A | 9/1999 |
| WO | 00/66985 A1 | 11/2000 |
| WO | 00/71991 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2011/108369 A1 | 9/2011 |
| WO | 2012/014778 A1 | 2/2012 |
| WO | 2013-024650 A1 | 2/2012 |
| WO | 2012/050011 A1 | 4/2012 |
| WO | 2012-144528 A1 | 10/2012 |

OTHER PUBLICATIONS

F.J. Meyer-Almes, "A new Method for Use in Molecular Diagnostics and High Throughput Pharemaceutical Screening based on Fluorescence Correlation Spectroscopy", Nanoparticle Immunoassays, R. Ridger, edit., Springer, Berlin, 2000, pp. 204-224.

N. Kato, et al., "A single molecule analyzer that enables new analysis of DNA and proten interactions", Gene Medicine, 2002, vol. 6, No. 2, pp. 271-277.

P. Kask, et al., "Fluorescence-intensity distribution analysis and its application in biomolecular detection technology", PNAS, 1999, vol. 96, No. 24, pp. 13756-13761.

International Search Report Dated Feb. 14, 2012, Issued in Corresponding Application No. PCT/JP2012/051175.

International Search Report of PCT/JP2011/053481, mailing date Mar. 29, 2011.

Park et al., "Counting the Number of Fluorophores Labeled in Biomolecules by Observing the Fluorescence-Intensity Transient of a Single Molecule", Bulletin of the Chemical Society of Japan, vol. 78, No. 9, p. 1612-1618, Aug. 30, 2005.

U.S. Office Action mailed Apr. 2, 2013, issued in related U.S. Appl. No. 13/596,280.

P. Kask et al., "Two-Dimensional Fluorescence Intensity Distribution Analysis: Theory and Applications", Biophysical Journal, vol. 78, pp. 1703-1713, (2000).

Chinese Office Action dated Aug. 13, 2013, issued in related Chinese application No. 201180011655.3 with translation (16 pages).

International Search Report dated Mar. 29, 2011, issued in related PCT/JP2011/053483.

English Translation of International Preliminary Report on Patentability (PCT/IPEA/409) issued in related PCT/JP2011/053483.

Chinese Office Action dated Aug. 9, 2013, issued in related Chinese application No. 201180011640.7 with translation (16 pages).

International Search Report dated Mar. 29, 2011, issued in related PCT/JP2011/053482.

International Preliminary Report on Patentability (PCT/IPEA/409) issued in related PCT/JP2011/053482.

U.S. Office Action dated Jan. 3, 2013, issued in related U.S. Appl. No. 13/597,825.

Chinese Office Action dated Feb. 7, 2013, issued in related Chinese application No. 201180011644.5 with translation (18 pages).

Extended European search report dated Mar. 28, 2013, issued in related EP application No. 11750481.

Japan Office Action dated Dec. 18, 2012, issued in related JP application No. 2012-503060 with translation (6 pages).

Written Opinion of International Searching Authority (PCT/ISA/237) dated Mar. 29, 2011, issued in related PCT/JP2011/053481.

International Preliminary Report on Patentability (PCT/IPEA/409) issued in related PCT/JP2011/053481.

(56) References Cited

OTHER PUBLICATIONS

Goodwin et al. "Rapid sizing of individual fluorescently stained DNA fragments by flow cytometry," Nucleic Acids Research, 1993, vol. 21, No. 4 pp. 803-806.
Keller et al. "Single-Molecule Fluorescence Analysis in Solution," Applied Spectroscopy, 1996, vol. 50, No. 7, pp. 12A-32A.
Lee et al. "Laser-Induced Fluorescence Detection of a Single Molecule in a Capillary," Analytical Chemistry, Dec. 1, 1994, vol. 66, No. 23, pp. 4142-4149.
Li et al. "Ultrasensitive Coincidence Fluorescence Detection of Single DNA Molecule," Analytical Chemistry, Apr. 1, 2003, vol. 75, No. 7, pp. 1664-1670.
Nie et al. "Probing Individual Molecules with Confocal Fluorescence Microscopy," Science, Nov. 11, 1994, vol. 266, pp. 1018-1021.
Tahari, "Fluorescence Correlation Spectroscopy: Ultrasensitive Detection in Clear and Turbid Media," University of Illinois, 2005, pp. 1-88.
Wu et al. "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, pp. 2157-2159.
Itoh et al. "A New Method for Detection of Influenza Viruses by Single Particle-Recognition Based on the Principle of Fluorescence Correlation Spectroscopy," Chemistry and Biology, 2009, vol. 47, No. 12, pp. 823-830.
Carlsson K et al: "Three-dimensional microscopy using a confocal laser scanning microscope", Optics Letters, The Optical Society, vol. 10, No. 2, Feb. 1, 1985, pp. 53-55, XP007922413, ISSN: 0146-9592.
U.S. Office Action dated Oct. 4, 2013, issued in related U.S. Appl. No. 13/596,243.
International Search Report for PCT/JP2012/0697692, Mailing Date of Aug. 14, 2012.
International Search Report dated Aug. 28, 2012 issued in corresponding application No. PCT/JP2012/068947.
Extended European Search Report dated Oct. 20, 2014, issued in related European Patent No. 12770835.2 (10 pages).
Chinese Office Action dated Oct. 10, 2014, issued in corresponding Chinese Application No. 201280005999.8; w/English Translation. (20 pages).
Extended European Search Report dated Mar. 31, 2015, issued in European Patent Application No. 12823870.6 (15 pages).
Extended European Search Report dated Apr. 10, 2015, issued in European Patent Application No. 12827023.8 (13 pages).
Office Action dated Mar. 25, 2015, issued in Chinese Patent Application No. 201280039905.9, with English translation (34 pages).
Office Action dated Apr. 24, 2015, issued in Chinese Patent Application No. 201280041770.X, with English translation (27 pages).
Office Action dated Jun. 1, 2015, issued in Chinese Patent Application No. 201280005999.8 w/English translation (15 pages).
Non-Final Office Action dated Nov. 16, 2015, issued in U.S. Appl. No. 14/178,442.
Chinese Office Action dated Jan. 25, 2016, issued in Chinese Application No. 201280005999.8.
Non-Final Office Action dated Jun. 24, 2016, issued in related U.S. Appl. No. 14/188,375. (9 pages).
Chinese Office Action dated Aug. 2, 2016, issued in related Chinese application No. 201280005999.8.X; with English Translation.
Official Action dated Nov. 24, 2016, issued in EP Patent Application No. 12823870.6.
U.S. Final Office Action dated Dec. 29, 2016, issued in U.S. Appl. No. 14/188,375.
Office Action dated Feb. 17, 2017, issued in Chinese Application No. 201280005999.8, with English translation (19 pages).
Final Office Action dated May 25, 2017, issued in U.S. Appl. No. 14/188,375 (9 pages).
International Search Report dated Mar. 15, 2016, issued in PCT/JP2015/084490.
Extended European Search Report dated Oct. 2, 2017, issued in related European patent application No. 11750482.9.
Extended European Search Report dated Sep. 29, 2017, issued in related European patent application No. 11750483.7.
Final Office Action dated Nov. 1, 2017 for the related in U.S. Appl. No. 14/188,375.

\* cited by examiner

FIG.1A
FIG.1B
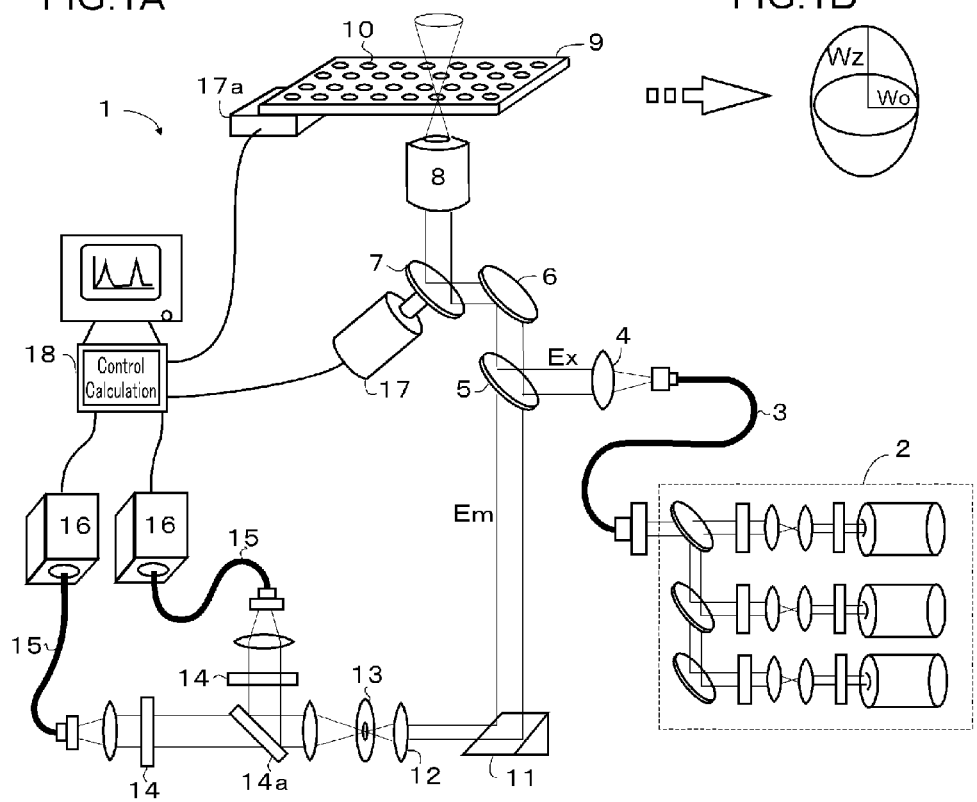
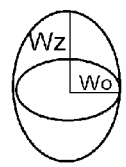
FIG.1C
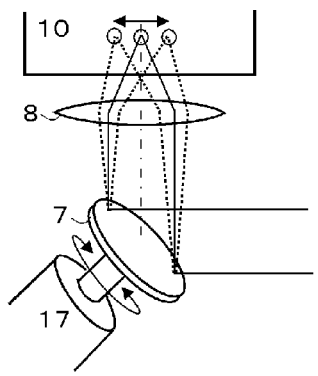

FIG.6A
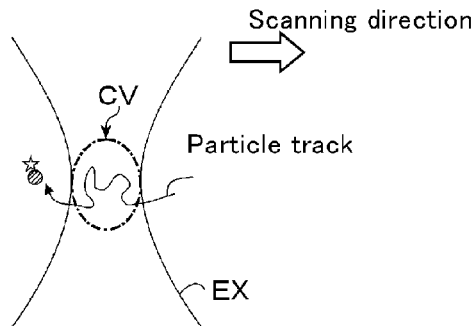
FIG.6B
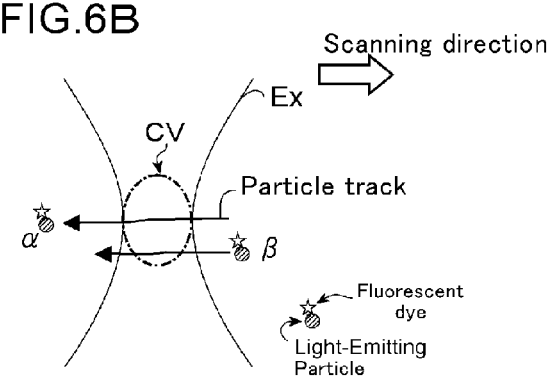
FIG.6C
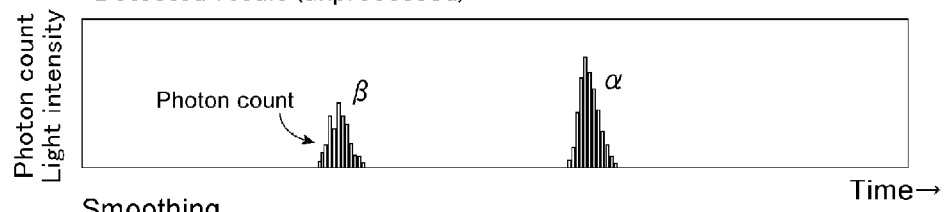
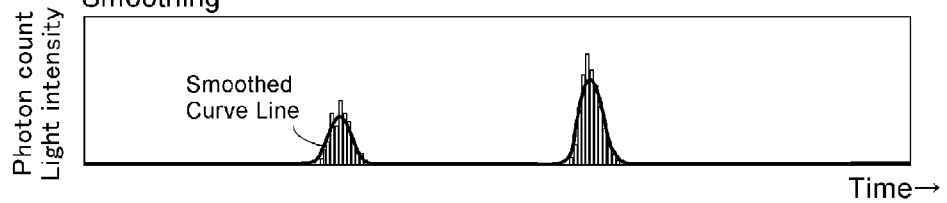
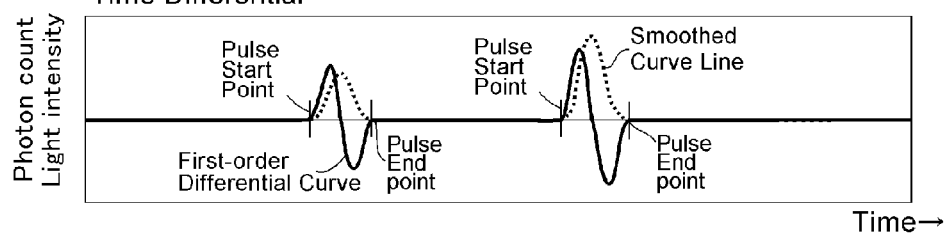
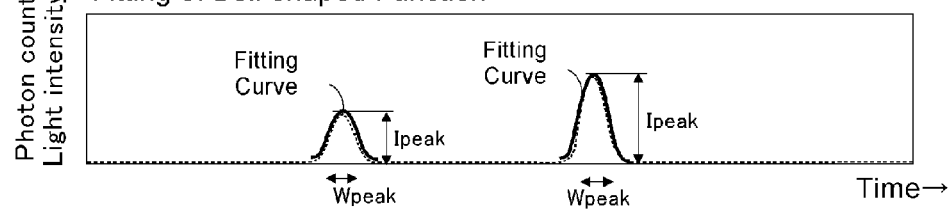

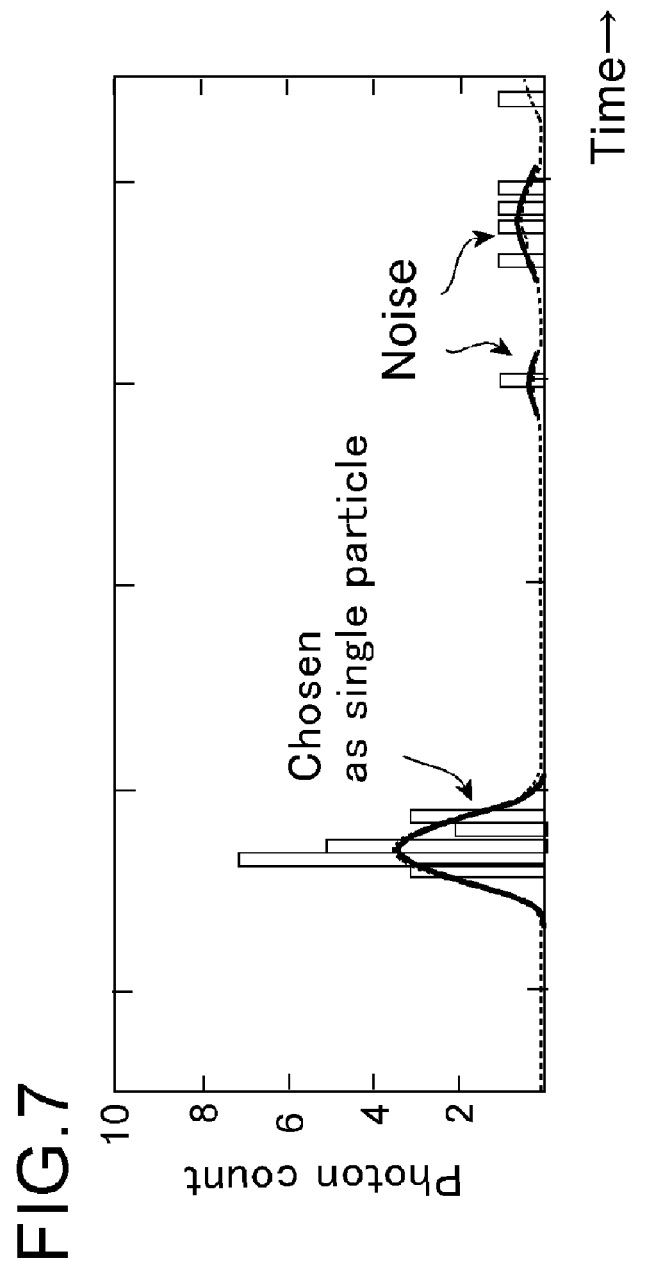

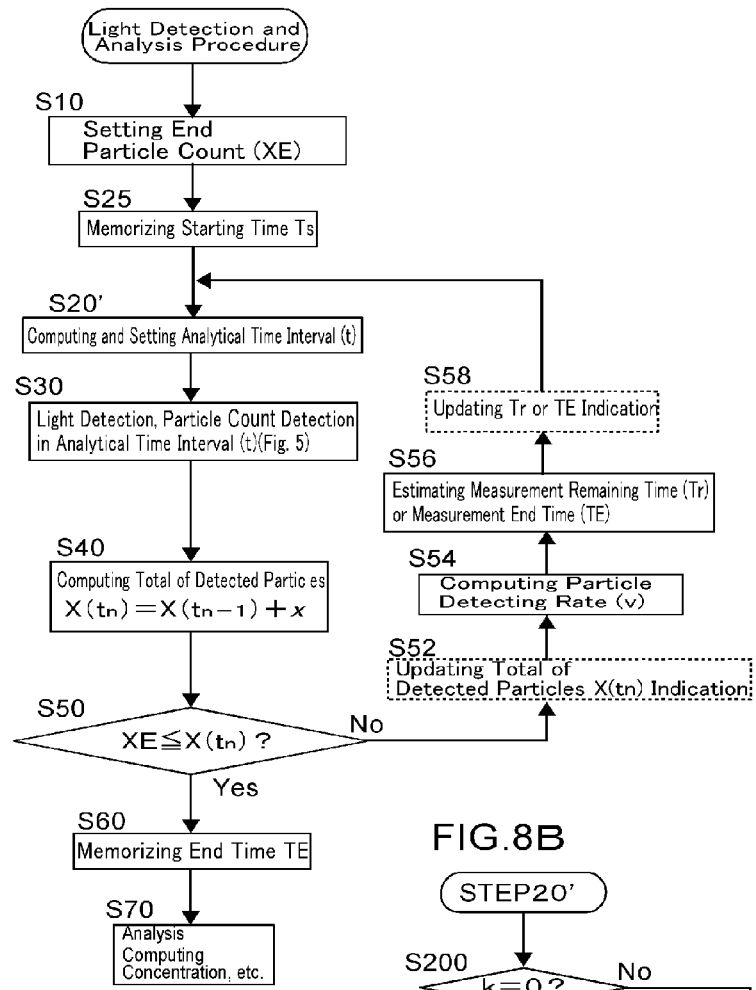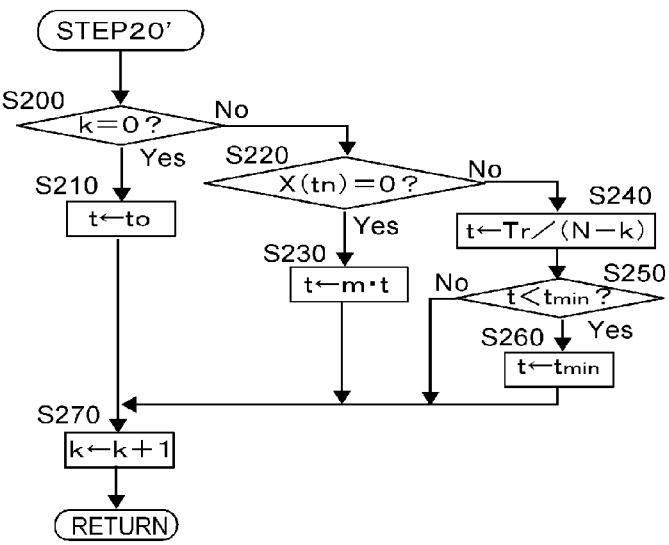

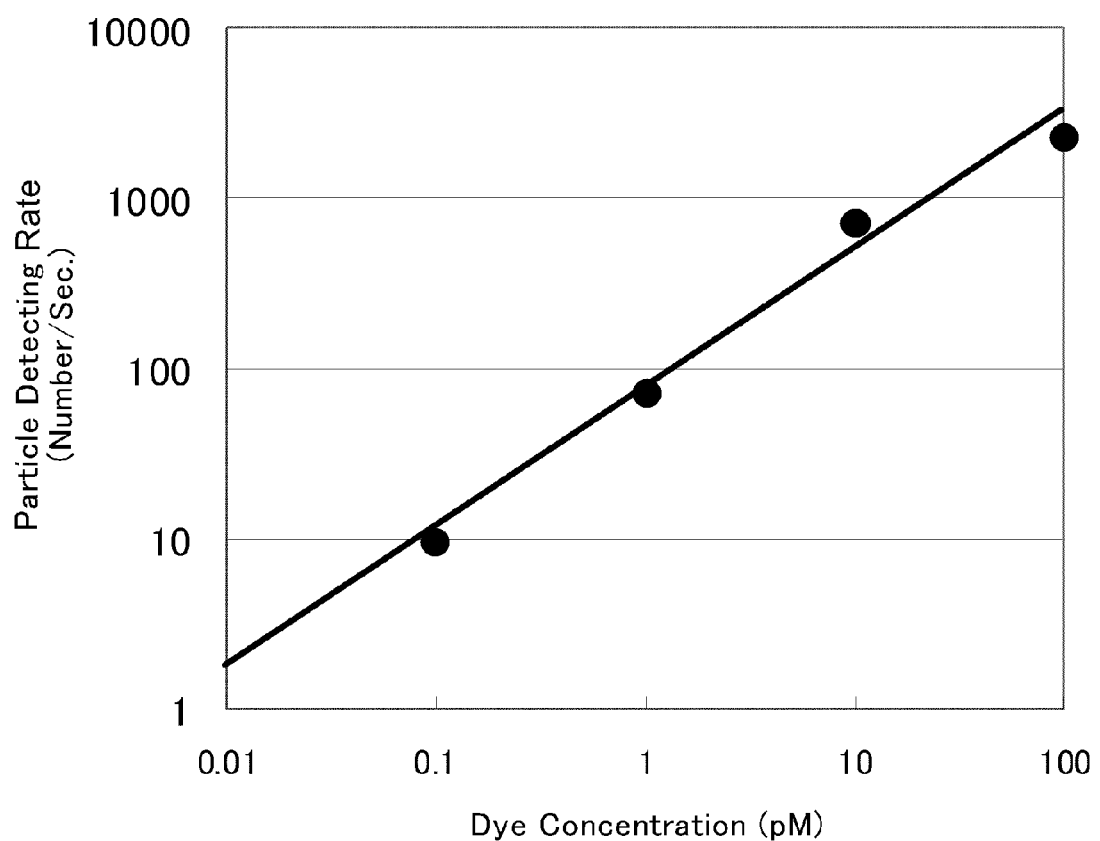

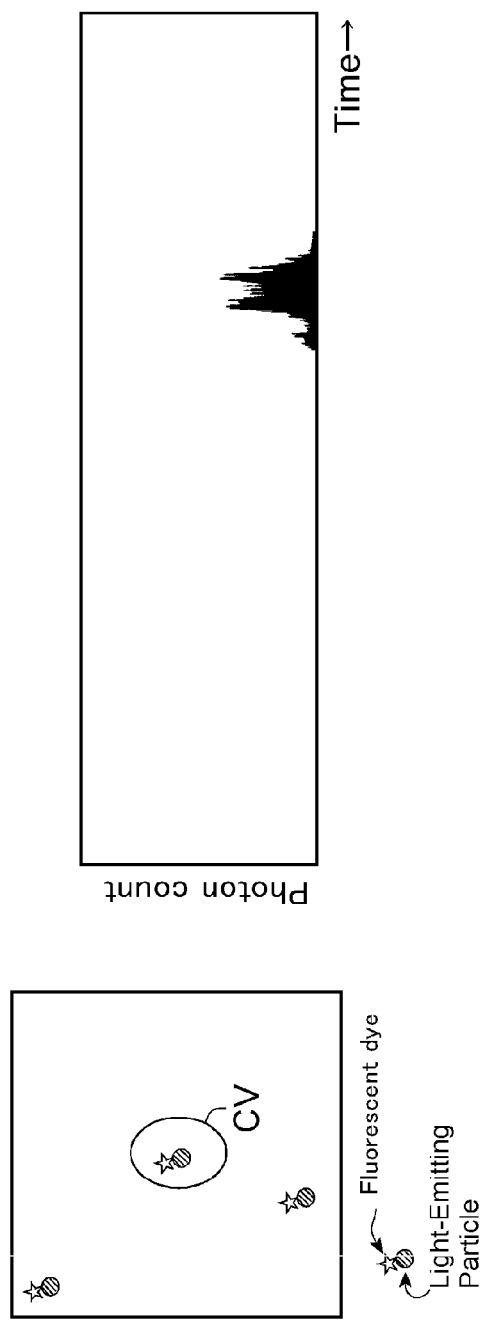
FIG.11A High Concentration (e. g. ~ 1nM)
FIG.11B Low Concentration (e. g. ~ 1pM)

OPTICAL ANALYSIS METHOD AND OPTICAL ANALYSIS DEVICE USING THE DETECTION OF LIGHT FROM A SINGLE LIGHT-EMITTING PARTICLE

TECHNICAL FIELD

This invention relates to an optical analysis method and an optical analysis device capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to a method and a device of detecting individually the light from a single particle which emits light, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label or light-emitting probe has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of $\mu L$), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.

Non-patent document 3: Noriko Kato, et al. "Gene medicine", Vol. 6, No. 2, pages 271-277.

Non-patent document 4: P. Kask, K. Palo, D. Ullmann, K. Gall PNAS 96, 13756-13761 (1999)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light the statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably at a level so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

By the way, in detecting a light-emitting particle in a sample solution individually and determining its concentration or other characteristics by the above-mentioned "scanning molecule counting method", it is preferable to detect the number of light-emitting particles which gives the accuracy required in the result. For instance, in determining a light-emitting particle concentration in a sample solution by the scanning molecule counting method, there are conducted processes of counting the number of individually detected light-emitting particles and dividing the counted number with the total volume of the passing region of a light detection region during a measuring time (the time of performing the light detection). In that case, the light-emitting particles are dispersed at random in the sample solution, and therefore, in order to determine its concentration at high accuracy, the count number of the light-emitting particles should have reached a number so sufficient that its scattering will be small. The count number of the light-emitting particles increases during much shorter time as the light-emitting particle concentration in the sample solution increases, and accordingly, the measuring time to achieve the detection of light-emitting particles of the number which gives the requested accuracy becomes shorter as the light-emitting particle concentration becomes high. In the other words, in determining a concentration or other characteristics of light-emitting particle in a sample solution by the "scanning molecule counting method", the necessary measuring time differs depending on the light-emitting particle concentrations.

However, when the concentration of a light-emitting particle to be an observation object in an sample solution is unknown, the measuring time, taken for the detection of light-emitting particles of the number which gives a requested accuracy, is unknown, and thus, the measuring time will be set so that the detection of light-emitting particles of the number which gives the requested accuracy will be achieved even at a low light-emitting particle concentration. In that case, for a sample solution with a high light-emitting particle concentration, the measuring time may become long more than needed. Further, when the detection of light-emitting particles is conducted for a constant measuring time irrespective of light-emitting particle concentrations, the scattering can become small in the result of a high light-emitting particle concentration while the scattering can become large in the result of a low light-emitting particle concentration.

Thus, one object of the present invention is to provide a new method and device which can complete the detection of light-emitting particles of the number which achieves an accuracy required in a result in as short a time as possible in the above-mentioned "scanning molecule counting method."

Further, another object of the present invention is to provide a new method and device which can suppress the scattering in a result small, irrespective of concentrations of light-emitting particles to be observation objects, in the above-mentioned "scanning molecule counting method."

Moreover, the other object of the present invention is to provide a new method and device which can optimize the measuring time in the above-mentioned "scanning molecule counting method" in accordance with the concentration of a light-emitting particle to be an observation object.

Solution to Problem

According to the present invention, the above-mentioned object is achieved by a method of detecting and analyzing light from a light-emitting particle dispersed and moving at random in a sample solution using an optical system of a confocal microscope or a multiphoton microscope, characterized by comprising: a light detection region moving step of moving a position of a light detection region of the optical system of the microscope in the sample solution by changing an optical path of the optical system; a light detecting step of detecting light from the light detection region with moving the position of the light detection region in the sample solution; and a light-emitting particle detecting step of detecting a signal from each light-emitting particle individually from the detected light; wherein said three steps are repeated until the number of the signals from the light-emitting particles reaches a predetermined number and a concentration of the light-emitting particle in the sample solution is determined based on a time taken for the number of the signals from the light-emitting particles to reaches the predetermined number.

In the structure of the present invention, a light-emitting particle "dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope.). Further, in the followings in this specification, "a signal" means "a signal expressing light from a light-emitting particle" unless noted otherwise.

As understood from the above, in the basic structure of the present invention, i.e., the scanning molecule counting method, the light detection is sequentially performed while the position of a light detection region is moved in a sample solution, namely, while the inside of the sample solution is scanned with the light detection region. Then, when the moving light detection region encompasses a randomly moving light-emitting particle, the light from the light-emitting particle is detected by a light detector, and thereby, it is expected that the existence of one particle will be detected. Thus, in the sequentially detected light, a signal indicating the light from a light-emitting particle is individually detected, and thereby, the individual existences of light-emitting particles are detected one by one, and accordingly, diverse information on the condition of the particle in the solution will be acquired. When this series of steps, i.e., the light detection region moving step, the light detecting step and the light-emitting particle detecting step are performed for a certain fixed measuring time irrespective of the light-emitting particle concentrations in a sample solution, as noted above, the scattering in the numbers of the detected light-emitting particles differs depending upon the light-emitting particle concentrations, and at a high light-emitting particle concentration, the measuring time may become long more than needed, while, at a low light-emitting particle concentration, the detection of the number of light-emitting particles which achieves the accuracy required in the measurement may not be achieved.

Thus, in the inventive method, the light detection region moving step, light detecting step and light-emitting particle detecting step are not performed for a certain fixed measuring time, but repeated until the number of the signals from the light-emitting particles reaches a predetermined number as noted above. Then, the time taken to detect the predetermined number of light-emitting particles is measured, and based on the time taken for this number of the signals from light-emitting particles to reach the predetermined number, a light-emitting particle concentration in a sample solution is determined. According to this structure, the number of detected light-emitting particles will reach a predetermined number for a shorter time as the light-emitting particle concentration becomes higher, and thus, the shortening of the measuring time for a high light-emitting particle concentration sample solution is expected, and also, the measurement for a low light-emitting particle concentration sample solution will be performed with a sufficient time. That is, according to the above-mentioned structure, the measuring time is optimized according to the light-emitting particle concentration. Further, by setting the predetermined number to the number which attains an accuracy required in a result, the scattering in the time taken for the detection of the predetermined number of light-emitting particles for a low light-emitting particle concentration sample solution or an arbitrary result derived therefrom will be suppressed small, so that it becomes possible to make the accuracy of the result sufficient.

In the structure of the above-mentioned inventive method, since the light-emitting particle concentration is reflected in the time taken for the number of the signals from the light-emitting particles to reach the predetermined number, it should be understood that the concentration is determinable based upon the time taken for the number of the signals from the light-emitting particles to reach the predetermined number. Concretely, a light-emitting particle concentration may be computed using an arbitrary function of a time taken for the number of signals from light-emitting particles to reach a predetermined number. For example, since a detection rate of light-emitting particles (detected number per unit time), determined based on the number of detected light-emitting particles (namely, the predetermined number) and a time taken for the number of the signals from the light-emitting particles to reach the predetermined number, is proportional to a light-emitting particle concentration, it may be used advantageously.

Moreover, as understood from the explanation of the column of Embodiments, in the series of the above-mentioned steps, in which the light from a sample solution is detected in the light detection region moving step and the light detecting step, and an existence of a light-emitting particle is detected from acquired data in the light-emitting particle detecting step, there is required a process to specify a signal of a light-emitting particle with excluding noises out of the acquired data. In a case of performing the light detection for a certain fixed measuring time, this process can be done by analyzing the acquired data collectively after the completion of the light detection for a fixed measuring time. However, in the case that the detection of light-emitting particles is performed until the number of the signals from the light-emitting particles reaches a predetermined number, it is required to detect a signal from a light-emitting particle during the light detection region moving step and light detecting step. Then, in the structure of the above-mentioned inventive method, the light detection region moving step, light detecting step and light-emitting particle detecting step may be repeated every predetermined interval in a period until the number of the signals from the light-emitting particles reaches the predetermined number. This predetermined interval may be fixed or may be modified based on the number of the light-emitting particles detected so far during the period until the number of the signals from the light-emitting particles reaches the predetermined number. Especially in the latter case, it becomes possible to adjust the predetermined interval according to the detecting condition of light-emitting particles in a sample solution at the time of repeating the series of the above-mentioned steps after the measurement has been actually started, and thus, it becomes possible to make the measuring time more optimized.

Furthermore, for one of embodiments of the above-mentioned inventive method, there may be conducted a step of estimating the time taken for the number of the signals from the light-emitting particles to reach the predetermined number based on the number of the light-emitting particles detected so far in the period until the number of the signals from the light-emitting particles reaches the predetermined number. Concretely, for instance, after starting the detection, a detection rate of light-emitting particles is determined based on the elapsed time after starting the detection and the number of the light-emitting particles detected so far, and from this light-emitting particle detection rate, it becomes possible to estimate the time taken for the number of the signals from the light-emitting particles to reach the predetermined number. According to this structure, when the measuring time is completed will become predictable, which is information convenient for an experimenter.

By the way, with respect to the moving of the position of the light detection region in the above-mentioned inventive structure, the moving speed of the position of the light detection region in a sample solution may be appropriately changed based on the characteristic of a light-emitting particle or its concentration in the sample solution. Especially when the moving speed of the light detection region becomes high, the light amount obtained from one light-emitting particle will be reduced, and therefore, it is preferable to appropriately change the moving speed of the light detection region in order to measure the light from one light-emitting particle precisely or sensitively.

Furthermore, with respect to the above-mentioned moving of the position of the light detection region, the moving speed of the position of the light detection region in the sample solution is preferably set to be higher than the diffusional moving velocity of a light-emitting particle (the average moving speed of a particle owing to the Brownian motion). As explained above, in the inventive method, the light-emitting particle will be detected individually by detecting the light emitted from a light-emitting particle encompassed in the light detection region. However, when a light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of the light-emitting particle, and thereby it becomes possible to make one light-emitting particle correspond to one signal. In this regard, since the diffusional moving velocity differs depending upon light-emitting particles, it is preferable that the moving speed of the light detection region can be changed appropriately according to the characteristics of the light-emitting particle as described above.

The changing of the optical path of the optical system for moving the position of the light detection region may be done in an arbitrary way. For example, the position of the light detection region may be changed by changing the optical path using a galvanomirror employed in the laser scan type optical microscope. The movement route of the position of the light detection region may be set arbitrarily, for example, which is selectable from circular, elliptical, rectangular, straight and curvilinear ones. In this connection, in the present invention, since the position of the light detection region is moved by changing the optical path of an optical system, the movement of the light detection region is quick without substantial generation of mechanical vibration and hydrodynamic effect in the sample solution, and therefore, the measurement of light can be performed under a stable condition without dynamic action affecting the light-emitting particle in the sample solution (without artifact) (For example, when a flow is generated in the sample, not only making the flow velocity always uniform is difficult, but also the device structure would become complicated, and furthermore, not only the required sample amount is substantially increased, but also it is possible that light-emitting particles or other substances in a solution would deteriorate or be denaturalized by the hydrodynamic action of the flow.). Further, since no structure for flowing a sample solution is required, the measurement and analysis can be conducted with a small amount of the sample solution (at the level of one to several tens of μL) similarly to FCS, etc.

The above-mentioned inventive method is realized with a new optical analysis device which can detect the light of each light-emitting particle with moving the position of a light detection region in a sample solution. Thus, in another aspect of the present invention, the above-mentioned object of the present invention is achieved by an optical analysis device which detects light from a light-emitting particle dispersed and moving at random in a sample solution using an optical system of a confocal microscope or a multiphoton microscope, characterized by comprising a light detection region mover which moves a position of a light detection region of an optical system of the microscope in the sample solution by changing an optical path of the optical system; a light detector which detects light from the light detection region; and a signal processor which detects individually a signal from each light-emitting particle detected in the light detector with moving the position of the light detection region in the sample solution, wherein the device repeats the moving of the position of the light detection region of the optical system with the light detection region mover, the detecting of the light from the light detection region with the light detector and the detecting of the signal from the light-emitting particle with the signal processor until the number of the signals from the light-emitting particles detected with the signal processor reaches a predetermined number, and the device determines a concentration of the light-emitting particle in the sample solution based on a time taken for the number of the signals from the light-emitting particles to reach the predetermined number.

Also in the above-mentioned inventive device, the light-emitting particle concentration may be determined based on a detection rate of the light-emitting particles determined based on the time taken for the number of the signals from the light-emitting particles to reach the predetermined number. Further, the above-mentioned inventive device may be designed to repeat the moving of the position of the light detection region of the optical system with the light detection region mover, the detecting of the light from the light detection region with the light detector and the detecting of the signals from the light-emitting particles with the signal processor every predetermined interval in a period until the number of the signals from the light-emitting particles reaches the predetermined number. The predetermined interval may be an arbitrarily fixed interval, or there may be provided a modifier for modifying the predetermined interval based on the number of the light-emitting particles detected so far in the period until the number of the signals from the light-emitting particles reaches the predetermined number, so that the optimization of the predetermined interval and the measuring time may be improved. Furthermore, in the above-mentioned inventive device, there may be provided an estimator for estimating the time taken for the number of the signals from the light-emitting particles to reach the predetermined number based on the number of the light-emitting particles detected so far in the period until the number of the signals from the light-emitting particles reaches the predetermined number, so that an experimenter can know the end time of the detection of the light-emitting particles. Especially for this, in the inventive device, there may be provided a measurement end time display which indicates the time until the number of the signals from the light-emitting particles reaches the predetermined number, the time being estimated based on the number of the signals from the light-emitting particles detected with the signal processor after starting the detection of the signals from the light-emitting particles, and/or a light-emitting particle detected number display which indicates the number of the signals from the light-emitting particles detected with the signal processor after starting the detection of the signals from the light-emitting particles, and thus, according to this structure, the experimenter can advantageously expect the end time of the detection of the light-emitting particles. In this regard, in the above-mentioned inventive device, preferably, the moving of the position of the light detection region with the light detection region mover may be performed at a predetermined velocity or at a velocity quicker than the diffusion moving velocity of the light-emitting particle, and the moving speed of the position of the light detection region may be set arbitrarily.

The optical analysis technique of the present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect Of Invention

Generally, according to the present invention, in the scanning molecule counting method which detects an existence of a light-emitting particle individually by scanning the inside of a sample solution with a light detection region in a confocal microscope or a multiphoton microscope, the optimization of the measuring time becomes possible depending upon a light-emitting particle concentration in the sample solution. Especially by setting the predetermined number to be reached by the number of the signals from the light-emitting particles to a number which attains an accuracy requested in a result of an arbitrary experiment or measurement, it is expected that an accurate detected result will be obtained irrespective of light-emitting particle concentrations even when an actual concentration is unknown. Moreover, according to this feature, it is expected that an accurate result is obtained through less trial and error in comparison with a case of carrying out light detection and light-emitting particle detection for a certain fixed measuring time, and thus, the reductions of the efforts, labors, time and/or expense required for experiments or measurements are expected. Furthermore, in the present invention, a light-emitting particle is detected individually and its concentration is determined, and therefore, even a light-emitting particle, whose concentration is relatively low in a sample solution so that light will be buried in the light from other light-emitting particles in a conventional method, becomes detectable and its existence becomes observable. This feature is expected to be used for applications to detection of products of reactions with a comparatively low reaction ratio or intermediate products of a relatively small number.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device with which the inventive optical analysis technique is realized. FIG. 1B is a schematic diagram of a confocal volume (an observation region of a confocal microscope). FIG. 1C is a schematic diagram of the mechanism for changing the direction of the mirror 7 to move the position of a light detection region in a sample solution.

FIGS. 2A and 2B are a schematic diagram explaining the principle of the light detection and a schematic diagram of the variation of the measured light intensity with time in the scanning molecule counting method consisting of a part of the present invention, respectively.

FIGS. 3A-3C are drawings explaining about the principle of the present invention, showing time series light intensity data obtained by the scanning molecule counting method for a certain sample solution (time change of light intensity). FIG. 3A schematically shows a light intensity data when the light-emitting particle concentration in a sample solution is low, and FIG. 3B schematically shows a light intensity data when the light-emitting particle concentration in a sample solution is high. FIG. 3 C is a drawing schematically showing a passing region of a light detection region CV.

Figure 2A:
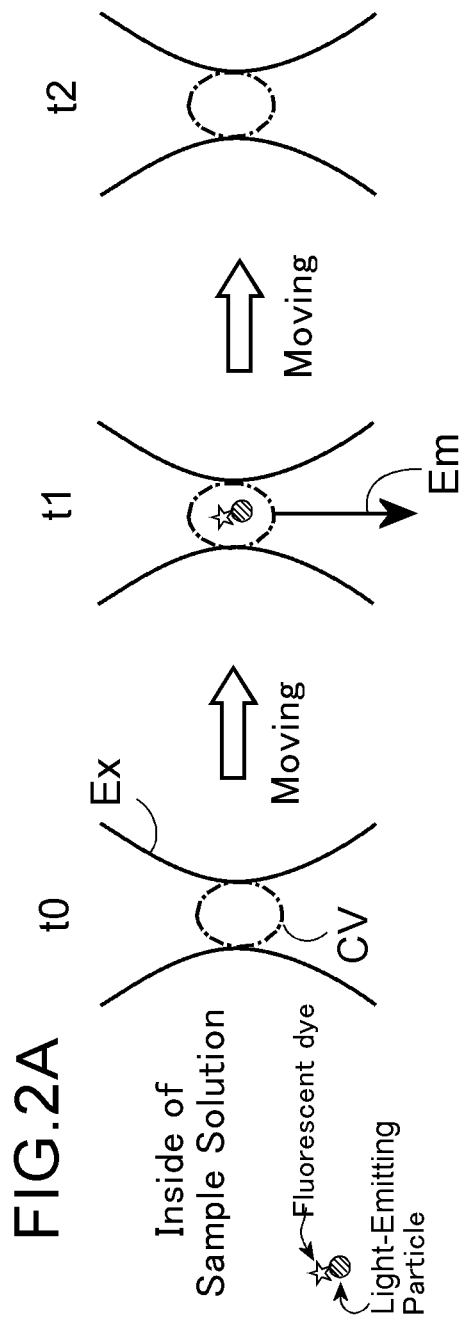

FIGS. 6 A and 6B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 6 C shows drawings explaining the example of the signal processing step of the detected signals in the procedure described in FIG. 5 for detecting the existence of a light-emitting particle from the measured time series light intensity data (change in time of photon count) in accordance with the scanning molecule counting method.

FIG. 7 shows examples of measured photon count data (bar graph); curves obtained by carrying out the smoothing of the data (dotted line); and Gauss functions fitted on the pulse existing region (solid line). In the drawing, the signals attached with "noise" are disregarded as signals due to noises or a contaminant.

FIG. 8A is a diagram showing in the form of a flow chart another embodiment of the procedures in the inventive optical analysis technique. FIG. 8B is a diagram showing in the form of a flow chart an example of the setting and modification processes of the analytical time interval t, performed in step 20' of FIG. 8A.

Figure 9A:
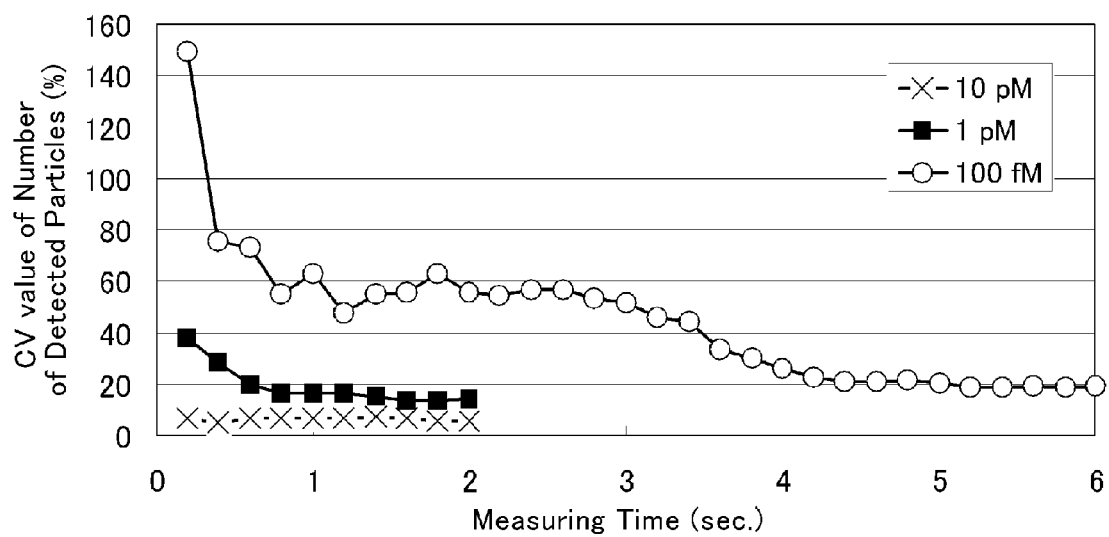
Figure 9B:
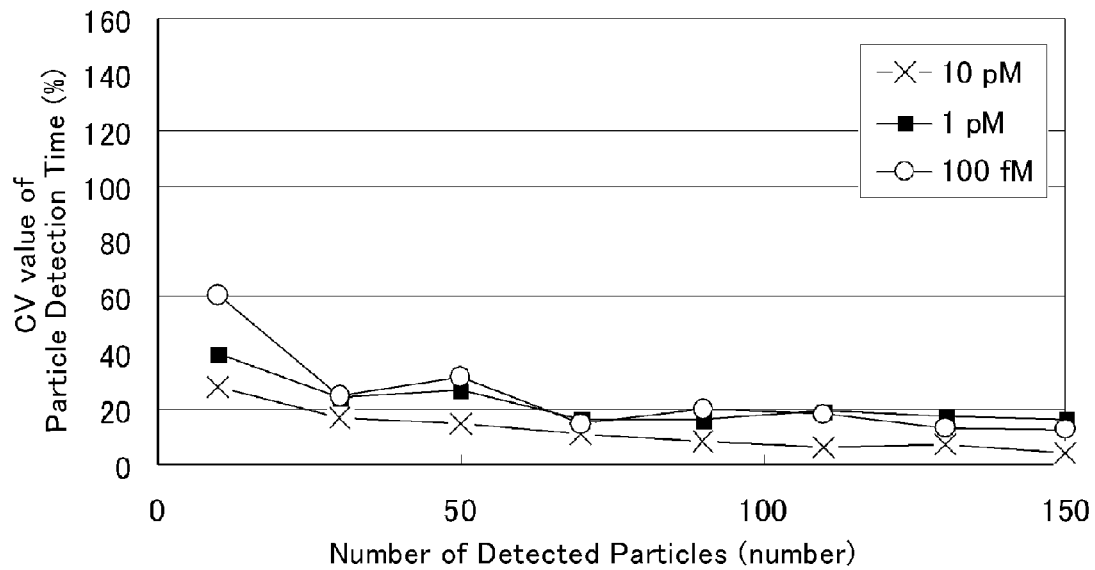

FIG. 9A shows time changes of scatterings (CV value) of numbers of light-emitting particles detected in 5 times of the trial experiments performed in accordance with the scanning molecule counting method for each of sample solutions containing fluorescent dye ATTO633 at 100fM, 1 µM and 10 µM, respectively. FIG. 9B shows variations of scatterings of the measuring times taken for the detections of the respective numbers of detected light-emitting particles (CV values of particle detection times) in 5 times of the trial experiments for each of the solutions of FIG. 9A against the number of the detected light-emitting particle.

FIG. 10 shows an experimental example of change of a detection rate of the light-emitting particles detected by the scanning molecule counting method against the light-emitting particle concentration (fluorescent dye ATTO633) in a sample solution.

FIGS. 11A-11B show examples of the time variation of the photon count (light intensity) obtained in a conventional optical analysis technique computing fluorescence intensity fluctuation, where FIG. 11A shows a case that the particle concentration is at a level providing a sufficient precision in the measurement, and FIG. 11B shows a case that the particle concentration in a sample is significantly lower than the case of FIG. 11A.

EXPLANATIONS OF REFERENCE NUMERALS

1—Optical analysis device (confocal microscope)
2—Light source
3—Single mode optical fiber
4—Collimating lens
5—Dichroic mirror
6, 7, 11—Reflective mirror
8—Objective
9—Micro plate
10—Well (sample solution container)
12—Condenser lens
13—Pinhole
14—Barrier filter
14a—Dichroic mirror for detection
15—Multi-mode optical fiber
16—Photodetector
17—Mirror deflector
17a—Stage position changing apparatus
18—Computer

DESCRIPTION OF EMBODIMENTS

In the followings, preferable embodiments of the present invention are described in detail.

Structure of Optical Analysis Device

In the basic structure, the optical analysis technique according to the present invention can be realized with an optical analysis device constructed by associating the optical system of a confocal microscope and a photodetector, enabling FCS, FIDA, etc., as schematically illustrated in FIG. 1A. Referring to FIG. 1A, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of µL of a sample solution is dispensed, and the laser light emitted from the objective 8 is focused in the sample solution in the sample container or well 10, forming a region having strong light intensity (excitation region). In the sample solution, light-emitting particles to be observed objects, which are typically molecules to which a light emitting label such as a fluorescent dye is attached, are dispersed or dissolved, and when a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13. In this regard, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the focal plane is blocked. The focal region of the laser light illustrated in FIG. 1B is a light detection region, whose effective volume is usually about 1-10 fL in this optical analysis device, which is called as "confocal volume". In the confocal volume, typically, the light intensity is spread in accordance with a Gaussian type or Lorentz type distribution having the peak at the center of the region, and the effective volume is a volume of an approximate ellipsoid bordering a surface where the light intensity is reduced to $1/e^2$ of the peak intensity. Then, the light having passed through the pinhole 13 passes the dichroic mirror 14a and transmits through the corresponding barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for optical analyses are executed in manners explained later. For the photodetector 16, preferably, a super high sensitive photodetector, usable for the photon counting, is used, so that the light from one light-emitting particle, for example, the faint light from one or several fluorescent dye molecule(s), can be detected.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C. This mirror deflector 17 may be the same as that of a galvanomirror device equipped on a usual laser scan type microscope. Also, in order to attain a desired moving pattern of the position of the light detection region, the mirror deflector 17 is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected.). In this regard, although not illustrated, the position of the light detection region may be moved in the vertical direction by moving the objective 8 up and down. As noted, according to the structure of changing the optical path of the optical system to move the position of the light detection region instead of moving the sample solution, neither mechanical vibration nor hydrodynamic action occur substantially in the sample solution, so that it becomes possible to eliminate the influence of a dynamic action on an object to be observed, achieving the stable measurement.

Also, for an additional structure, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18.

In the case that a light-emitting particle emits light by multiple photon absorption, the above-mentioned optical system is used as a multiphoton microscope. In that case, since the light is emitted only from the focal region of the excitation light (light detection region), the pinhole 13 may be removed. When a light-emitting particle emits light owing to phosphorescence or scattered light, the above-mentioned optical system of the confocal microscope is used as it is. Further, in the case that a light-emitting particle emits light owing to a chemiluminescence or bioluminescence phenomenon without excitation light, the optical system 2-5 for generating excitation light may be omitted. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, two or more photodetectors 16 may also be provided so as to detect the lights from light-emitting particles of two or more kinds having different light-emitting wavelengths, if contained in a sample, separately depending upon the wavelengths.

The Principle of the Present Invention

As described in the column of "Summary of Invention", briefly, in the "scanning molecule counting method" which detects light from a light-emitting particle one by one with a confocal microscope (or multiphoton microscope) as described above, the inventive method is designed to repeat the moving of a light detection region, the detecting of light and the detecting of a light-emitting particle until the number of the signals from the light-emitting particles reaches a predetermined number, and determine a light-emitting particle concentration in a sample solution based on the time taken for the number of the signals from the light-emitting particles to reach the predetermined number. In the following, the principles of the scanning molecule counting method and the determination of a light-emitting particle concentration in the present invention are explained.

1. Principle of Scanning Molecule Counting Method

Spectral analysis techniques, such as FCS, FIDA, etc., are advantageous in that the required sample amount is extremely small and a test can be performed promptly as compared with the conventional biochemical analytical techniques. However, in these spectral analysis techniques, such as FCS, FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement as schematically drawn in FIG. 11A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn on FIG. 11B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring time should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, such as its number density or concentration, even when the concentration of the light-emitting particle is lower than the level requested in the above-mentioned spectral analysis techniques, such as FCS and FIDA.

Figure 2B:
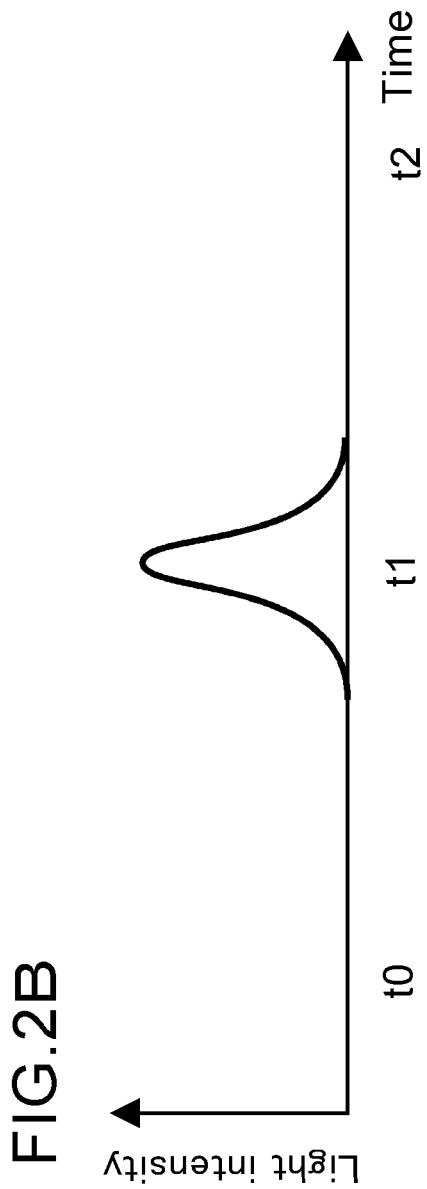

As the processes to be performed in the scanning molecule counting method, briefly speaking, the light detection, namely, measurement of light intensity, is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2. Then, for example, as in FIG. 2A, during the moving of the light detection region CV (in the drawing, time to -t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in FCS, FIDA, etc.

Figure 3A:
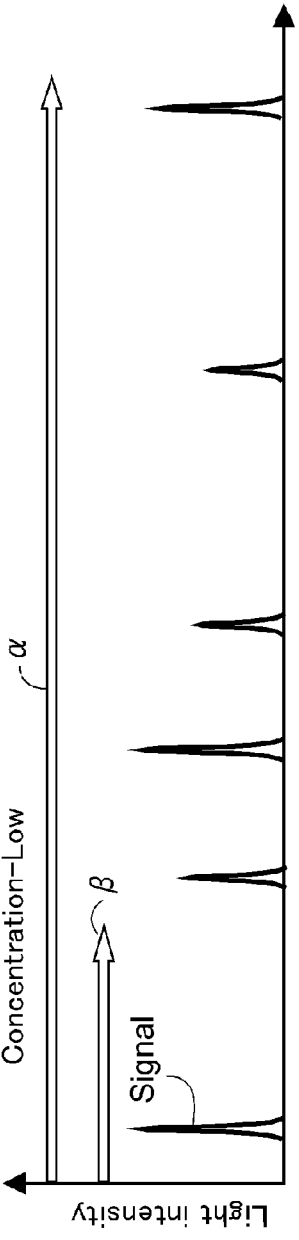
Figure 3B:
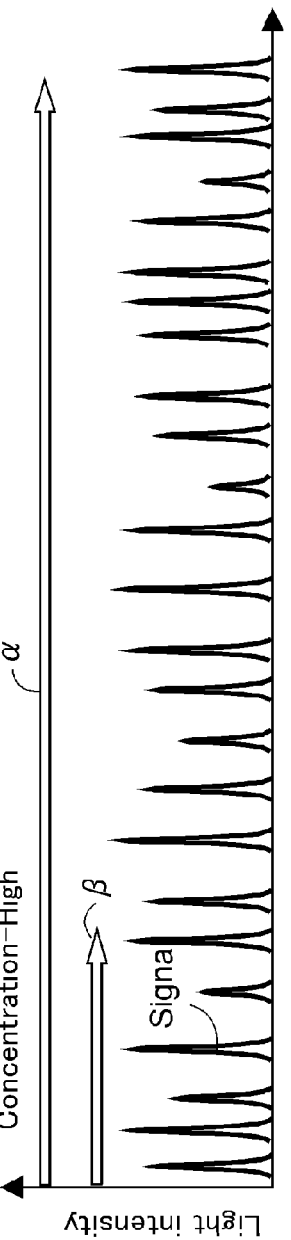
Figure 3C:
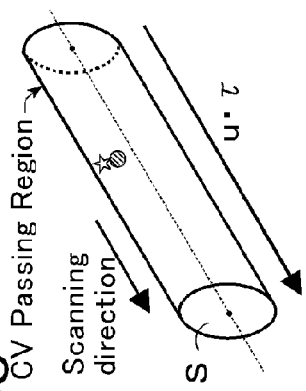

2. Principle of Determination of Light-emitting Particle Concentration according to the Present Invention In the scanning molecule counting method as described above, since light-emitting particles to be observation objects are dispersed at random in a sample solution, there is scattering in the number of detected light-emitting particles obtained in the light detection for a certain measuring time (the detected numbers differ in performed measurements). Accordingly, for determining, at an allowable or satisfiable accuracy, arbitrary characteristics derived with the number of detected light-emitting particles, such as a light-emitting particle concentration, etc. obtained by dividing the number of detected light-emitting particles by the volume of the passing region of the light detection region in a measuring time, the light intensity measurement should be performed for a time required to detect the number of light-emitting particles necessary for achieving the allowable or satisfiable accuracy. In this respect, the number of detected light-emitting particles obtained in a certain measuring time is to decrease as the light-emitting particle concentration becomes lower, and its scattering is to increase, and thus, in order to attain an allowable or satisfiable accuracy, a longer measuring time will be needed. For instance, referring to FIG. 3, in a case of detecting light-emitting particles for a certain measuring time a for a solution (A) of a comparatively low light-emitting particle concentration and a solution (B) of a comparatively high light-emitting particle concentration by the scanning molecule counting method, as understood from the comparison of FIGS. 3A and 3B, more signals of light-emitting particles will be detected in the time series light intensity data obtained for the solution of the comparatively high light-emitting particle concentration illustrated in FIG. 3B, as compared with the case of the solution of the comparatively low light-emitting particle concentration illustrated in FIG. 3A. Thus, for instance, when time α is needed as the measuring time for obtaining the number of detected light-emitting particles required for an allowable accuracy in the determination of a characteristic, such as a concentration, for the solution of FIG. 3A, time β will be sufficient for the solution of FIG. 3B. And if the measurement for the solution of FIG. 3A is performed only for time β, the scattering in the number of the detected light-emitting particles will become large, so that the error in the result of a concentration, etc. can become large to a non-allowable level.

However, in a case that a light intensity measurement is performed for a certain fixed measuring time under a condition that the light-emitting particle concentration in a sample solution is unknown, the measuring time will be set long enough for the case of a low light-emitting particle concentration. In this case, the light intensity measurement will be continued more than the time necessary to determine at allowable or satifiable accuracy a characteristic, such as concentration, in a case of a high light-emitting particle concentration in a sample solution. Moreover, when the light-emitting particle concentration in a sample solution is lower than a concentration expected by the experimenter and the set measuring time is insufficient, the error of the result will become large.

Then, in the present invention, instead of detecting the number of light-emitting particles from light intensity data obtained by performing a light intensity measurement (namely, a light detection) for a certain fixed measuring time, the light intensity measurement with moving a light detection region and the detection of the signals of light-emitting particles are repeated until the number of the signals from the light-emitting particles reaches a predetermined number; the time taken for the number of the signals from the light-emitting particles to reach the predetermined number is measured; and based on this time taken for the number of the signals from the light-emitting particles to reach the predetermined number, the light-emitting particle concentration is determined. According to this structure, the time taken for the light intensity measurement is shortened for a high light-emitting particle concentration in a sample solution, and it becomes possible to continue the light intensity measurement until the number of light-emitting particles, achieving an accuracy requested for a result (namely, the light-emitting particle concentration), is obtained for a low light-emitting particle concentration in a sample solution. And by setting the predetermined number which the number of the signals from light-emitting particles is to reach to the number of light-emitting particles which achieves an accuracy requested in a result, the number of the light-emitting particles which achieves the accuracy requested in the result will be reflected in the time taken for the number of the signals from the light-emitting particles to reach the predetermined number, and therefore, it is expected that the light-emitting particle concentration value determined based on the time has the allowable or satisfiable accuracy.

Concretely, a light-emitting particle concentration value determined according to the present invention is associated with a time taken for the number of signals from light-emitting particles to reach a predetermined number as follows: In a case that a light detection region is moved at a scanning speed u for time τ in a sample solution having a certain light-emitting particle concentration C, assuming that the cross sectional area of the light detection region is S (see FIG. 3C), the number X of detected light signals is:

$$X = CSu\tau N_A \quad (1)$$

where $N_A$ is the Avogadro's number. Thus, supposing it takes a time T for the number of the signals from the light-emitting particles to reach the predetermined number XE, the light-emitting particle concentration C is given as a function of the time T by:

$$C = XE/(STuN_A) \quad (2)$$

In this regard, in Expression (2), based on the time T, taken for the number of the signals from the light-emitting particles to reach the predetermined number XE, and the number XE of the detected light-emitting particles, a detection rate V of the particles per unit time is given by:

$$V=XE/T \quad (3),$$

and therefore, the light-emitting particle concentration C is represented by:

$$C=V/(SuN_A) \quad (4)$$

In this Expression (4), the light-emitting particle concentration C is proportional to the detection rate V in first-order so that the correspondence relation between the light-emitting particle concentration C and the detection rate V is intelligible, and therefore, in an actual experiment, the light-emitting particle concentration C may be determined using the detection rate V (see the following embodiment.).

Operation Processes

In the embodiment of an optical analysis in accordance with the present invention with the optical analysis device 1 as illustrated in FIG. 1A, concretely, there are conducted (1) preparation of a sample solution containing light-emitting particles; (2) measuring the light intensity of a sample solution and detecting and counting (a) light-emitting particle (s); and (3) an analysis, such as concentration calculation, etc.

(1) Preparation of a Sample Solution

The particle to be observed in the inventive optical analysis technique may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological particle (Typically, the sample solution is an aqueous solution, but not limited to this, and it may be an organic solvent or other arbitrary liquids.). Also, the particle to be observed may be a particle which emits light by itself, or may be a particle to which a light emitting label (a fluorescence molecule, a phosphorescence molecule, and a chemiluminescent or bioluminescent molecule) is attached in an arbitrary manner.

In this connection, since a light-emitting particle concentration in a sample solution can be determined in this embodiment, for example, a solution containing a component of a unknown concentration, a solution whose light-emitting particle concentration varies before and after a binding and dissociation reaction or an intermolecular interaction, etc. may be used as a sample solution, and the determination of a concentration of a component in a solution or the detection of the presence or absence or the degree of the progress of a reaction or an interaction may be done.

Figure 4:
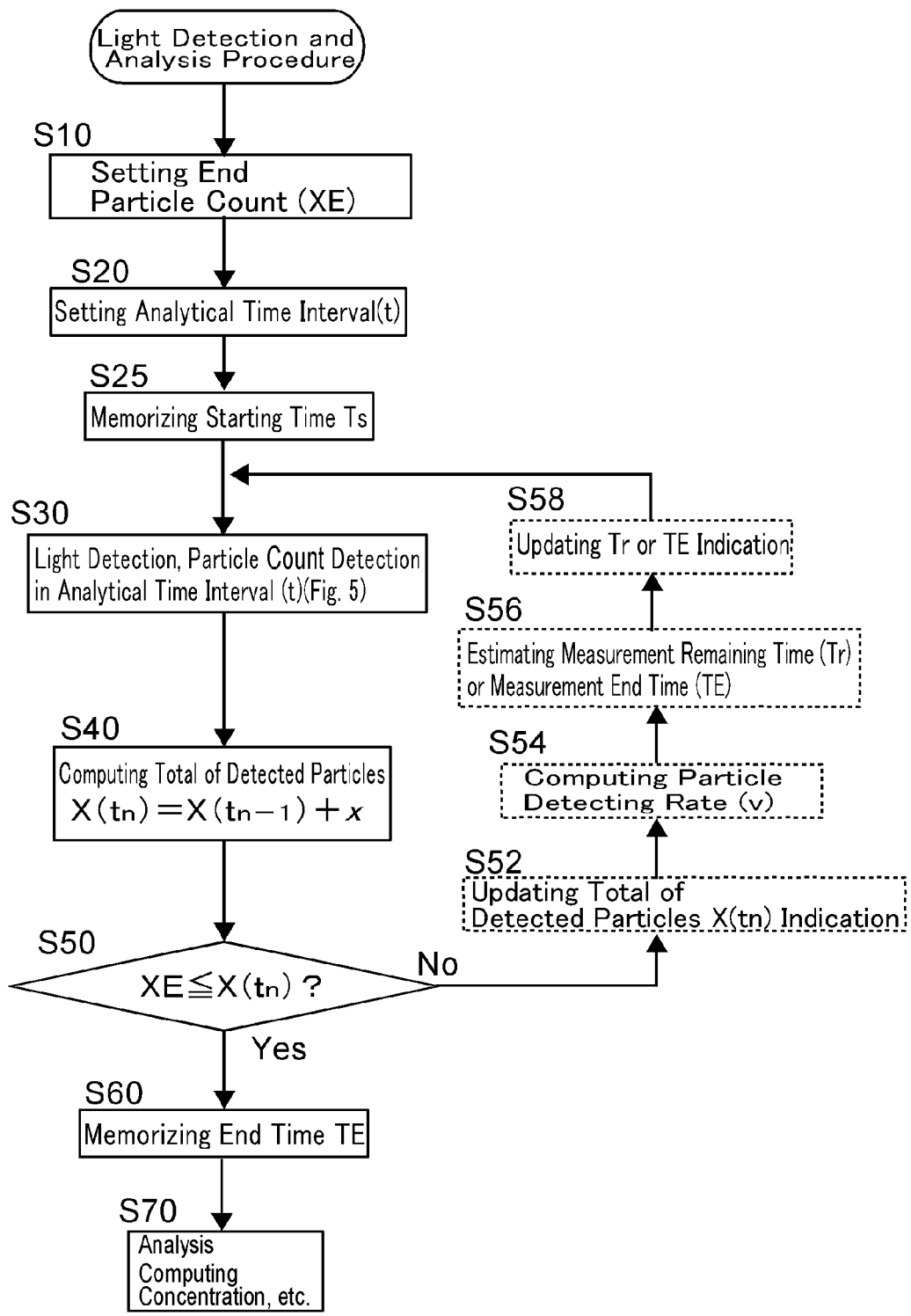
FIG. 4 is a diagram showing in the form of a flow chart one embodiment of the procedures in the inventive optical analysis technique.

(2) Measuring the Light Intensity of a Sample Solution, and Detecting and Counting Light-Emitting Particles FIG. 4 shows in the form of a flow chart one example of processes of light intensity measurement of a sample solution and detecting and counting light-emitting particles in the present embodiment performed with the optical analysis device 1 illustrated in FIG. 1A. In the example of this drawing, briefly, a series of processes of the moving of the position of a light detection region, the detecting of light from the light detection region, the detecting of signals from light-emitting particles and the counting of the signals of the detected light-emitting particles is repetitively performed every analytical time interval t (predetermined interval) until the number of the detected light-emitting particles X reaches the end particle count XE (the predetermined number that the number of light-emitting particles is to reach). In this regard, it should be understood that a series of processes and structures described below are realized by the processing operations of the computer 18. [The same in (3) Analysis, such as concentration calculation etc., and (4) Modified example of light intensity measurement of a sample solution and detecting and counting light-emitting particles]

(i) Initial Setting

In the operation processes, concretely, first, after dispensing a sample solution into the well(s) 10 of the micro plate 9 and putting it on the stage of the microscope, when a user inputs to the computer 18 a command of staring processes of a light intensity measurement and detecting and counting light-emitting particles, the computer 18 performs, as the initial setting, the setting of the end particle count XE(step 10) and the setting of the analytical time interval t (step 20). The end particle count XE and the analytical time interval t may be arbitrarily set by the user. In order to achieve an accuracy requested in a result value of a light-emitting particle concentration, the end particle count XE can be appropriately determined with reference to a result of a preliminary experiment using a solution having a known light-emitting particle concentration (see Embodiment described later). For the analytical time interval t, an arbitrary time interval enough shorter than the period until the number of light-emitting particles (X) reaches the end particle count (XE) after starting the process may be appropriately set, considering the processing speed, etc. of FIG. 5 as described later in the device 1. Further, for each of the end particle count XE and analytical time interval t, a value, determined beforehand with reference to a result of a preliminary experiment using a solution having a known light-emitting particle concentration, may be memorized in the device 1 so that the memorized value can be used automatically or by a user's choice.

(II) Detection of the Number of Light-Emitting Particles

When the setting of the end particle count XE and analytical time interval t has been made, the light intensity measuring process, the detection of signals of light-emitting particles from measured light intensity data and detection of the number of light-emitting particles x (step 30) in the analytical time interval t according to the scanning molecule counting method; and a process of accumulating the number of the light-emitting particles x detected in step 30 and computing the total number X(tn) of the light-emitting particles (step 40) are repetitively performed every analytical time interval t until the total number X(tn) of the light-emitting particles reaches the end particle count XE (step 50) as described below. In this regard, prior to the repetitive execution of processes of steps 30-50, the starting time Ts of a series of processes may be memorized (step 25). In the following, the processes of steps 30-50 will be explained in detail.

(a) Light Intensity Measurement

Figure 5:
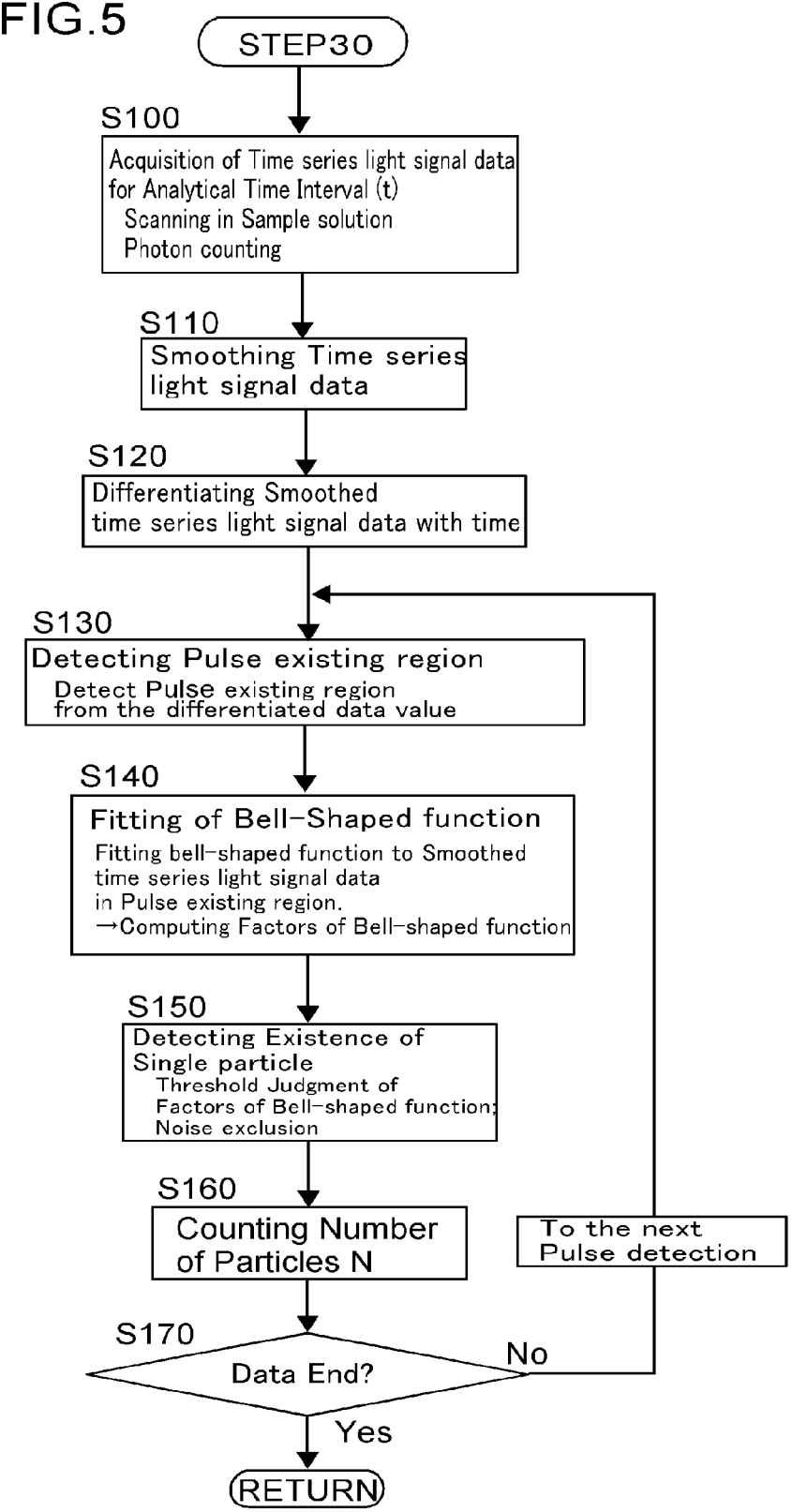
FIG. 5 is a diagram showing in the form of a flow chart an example of the procedures performed in each analytical time interval t in accordance with the scanning molecule counting method performed in step 30 of the flow chart of FIG. 4 or FIG. 8.

FIG. 5 shows an example of the process of step 30 in the form of a flow chart. With reference to this drawing, in the process of step 30, first, with driving the mirror deflector 17 to move the position of the light detection region within the sample solution (scan in the sample solution), a light intensity measurement is conducted for the analytical time interval t (FIG. 5-step 100). In this process, typically, according to programs (the process of changing the optical path in order to move the position of the light detection region in the sample solution, the processes of irradiating the light detection region with the excitation light (only when necessary)

and the process of detecting light from the light detection region during the moving of the position of the light detection region) memorized in a storage device (not shown), illuminating the light detection region in the sample solution with the excitation light (only when necessary) and measuring light intensity will be started. When the measurement was started, under the control of the operation process of the computer 18 according to the programs, from the light source 2, the light of the excitation wavelength of a light-emitting particle in the sample solution is emitted, and the mirror deflector 17 drives the mirror 7 (galvanomirror) to move the position of the light detection region in the well 10, and simultaneously with this, the photodetector 16 sequentially converts the received light into an electric signal and transmits it to the computer 18, which generates the time series light intensity data from the transmitted signals and store it in an arbitrary manner. The photodetector 16 is typically a super high sensitive photodetector which can detect an arrival of a single photon, and thus the detection of light may be the photon counting performed in the manner of measuring sequentially the number of photons which arrive at the photodetector for every predetermined unit time (BIN TIME), for example, every 10 μS, and accordingly the time series light intensity data will be a time series photon count data.

Regarding the moving speed of the position of the light detection region, in order to perform quantitatively precisely individual detection of a light-emitting particle from the measured time series light intensity data in the scanning molecule counting method, preferably, the moving speed of the position of the light detection region during the light intensity measurement is set to a value quicker than the moving speed in the random motion, i.e., the Brownian motion of a light-emitting particle. When the moving speed of the position of the light detection region is slower than the movement of a particle owing to the Brownian motion, the particle moves at random in the region as schematically drawn in FIG. 6A, whereby the light intensity changes at random (the excitation light intensity in the light detection region is reduced from the peak at the center of the region toward its outside.), so that it becomes difficult to determine a significant light intensity change corresponding to each light-emitting particle (a signal indicating light from a light-emitting particle). Then, preferably, as drawn in FIG. 6B, the moving speed of the position of the light detection region is set to be quicker than the average moving speed of a particle by the Brownian motion (diffusional moving velocity) so that the particle will cross the light detection region CV in an approximately straight line and thereby the profile of the change of the light intensity corresponding to each particle in the time series light intensity data becomes almost bell-shaped similarly to the excitation light intensity distribution as illustrated in the most upper row of FIG. 6C and the correspondence between each light-emitting particle and light intensity can be easily determined.

Concretely, the time Δτ required for a light-emitting particle having a diffusion coefficient D to pass through the light detection region of radius r (confocal volume) by the Brownian motion is given from Expression of the relation of mean-square displacement:

$$(2r)^2 = 6D \cdot \Delta\tau \quad (5)$$

as:

$$\Delta\tau = (2r)^2/6D \quad (6),$$

and thus, the velocity of the light-emitting particle moving by the Brownian motion (diffusional moving velocity) Vdif, becomes approximately $$V\text{dif} = 2r/\Delta\tau = 3D/r \quad (7)$$

Then, with reference to this, the moving speed of the position of the light detection region may be set to a value sufficiently quicker than Vdif. For example, when the diffusion coefficient of a light-emitting particle is expected to be about $D = 2.0 \times 10^{-10}$ m$^2$/s, Vdif will be $1.0 \times 10^{-3}$ μm/s, supposing r is about 0.62 μm, and therefore, the moving speed of the position of the light detection region may be set to its 10 times or more, e.g., 15 mm/s. In this regard, when the diffusion coefficient of a light-emitting particle is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(b) Detection of a Signal Corresponding to a Light-Emitting Particle

When the time series light intensity data of (a) light-emitting particles in the sample solution in the analytical time interval t is obtained by the above-mentioned processes, detection of a signal corresponding to light from a light-emitting particle on the light intensity data is performed in the computer 18 through processes in accordance with programs memorized in a storage device.

When the track of one light-emitting particle in its passing through the light detection region is approximately straight as shown in FIG. 6B, the light intensity variation in the signal corresponding to the particle in the time series light intensity data has a bell shaped profile reflecting the light intensity distribution in the light detection region (determined by the optical system) (see the most upper row of FIG. 6C). Thus, basically in the scanning molecule counting method, when the time width for which the light intensity exceeding an appropriately set threshold value continues is in a predetermined range, the signal having the profile of the light intensity may be judged to correspond to one particle having passed through the light detection region, and thereby one light-emitting particle is detected. And a signal whose time width for which the light intensity exceeding the threshold value continues is not in a predetermined range is judged as noise or a signal of a contaminant. Further, when the light intensity distribution in the light detection region can be assumed as Gaussian distribution:

$$I = A \cdot \exp(-2t^2/a^2) \quad (8),$$

and when the intensity A and the width a, computed by fitting Expression (8) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

As an example of more concrete operational methods of conducting the detection of light-emitting particles from time series light intensity, first, a smoothing treatment is performed to the time series light signal data (FIG. 6C, the most upper row "detected result (unprocessed)") (FIG.

5-step 110, FIG. 6C mid-upper row "smoothing"). Although the light emitted by a light-emitting particle is stochastic so that gaps will be generated in data values in minute time, such gaps in the data value can be disregarded by the smoothing treatment. The smoothing treatment may be done, for example, by the moving average method, etc. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the time series light intensity data after the smoothing treatment is computed (step 120). As illustrated in FIG. 6C, the mid-low row "time differential", in the time differential value of time series light signal data, the variation of the value increases at the time of the signal value change, and thereby, the start point and the end point of a significant signal can be determined advantageously by referring to the time differential value.

After that, a significant pulse signal is detected sequentially on the time series light intensity data, and it is judged whether or not the detected pulse signal is a signal corresponding to a light-emitting particle. Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 6C, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically Gauss function as in Expression (8), it may be Lorentz type function. And it is judged whether or not the computed parameters of the bell-shaped function are within the respective ranges assumed for the parameters of the bell-shaped profile drawn by a pulse signal detected when one light-emitting particle passes a light detection region, i.e., whether or not each of the peak intensity, the pulse width and the correlation coefficient of the pulse is within the corresponding predetermined range (step 150). Then, the signal, whose computed parameters of the bell-shaped function are judged to be within the ranges assumed in a light signal corresponding to one light-emitting particle, as shown in FIG. 7 left, is judged as a signal corresponding to one light-emitting particle, and thereby, one light-emitting particle will be detected and counted as one light-emitting particle (the particle count x is counted up one. Step 160). On the other hand, a pulse signal, whose computed parameters of the bell-shaped function are not within the assumed ranges, as shown in FIG. 7 right, is disregarded as noise.

The search, judgment and counting of (a) pulse signal(s) in the processes of the above-mentioned steps 130-160 are repetitively carried out in the whole region of the time series light signal data in the analytical time interval t. (Step 170). In this regard, the process of detecting individually signals of light-emitting particles from time series light intensity data may be conducted by an arbitrary way other than the above-mentioned way. When the search of (a) pulse signal(s) in all the time series light intensity data of the analytical time interval t is completed, step 30 is ended and step 40 is performed.

(c) Computation of the Total Number of Detected Light-Emitting Particles

Thus, when the number of light-emitting particles x in the time series light intensity data in the analytical time interval t is detected, the total number X ($t_n$) of the detected light-emitting particles is computed with $$X(t_n)=X(t_{n-1})+x \qquad (9)$$

(FIG. 4-step 40). Here, X ($t_{n-1}$) is the total number of the particles detected till the last analytical time interval t, and its initial value is 0. And, steps 30-40 are repeated every analytical time interval t until the total number of the detected light-emitting particles X(tn) reaches the end particle count XE, namely, $$X(t_n) \geq XE \qquad (10)$$

is established (step 50). Then, during the repeating of steps 30-50, when Expression (10) is established, the processes of the light intensity measurement of the sample solution and the detecting and counting of the light-emitting particles are ended. When the repetitive operations of steps 30-50 are completed, the end time TE may be memorized (step 60).

(d) Indication of the Number of Light-Emitting Particle and the Measurement End Time In the period of the repetitive execution of steps 30-50 in every analytical time interval t (until Expression (10) is established), the total number of the detected light-emitting particles X($t_n$) and/or the measurement end time TE or the measurement remaining time Tr may be indicated on a display, such as a monitor, etc. of the computer 18. According to this structure, it is advantageous in that a user can predict when an executed measurement is ended by seeing those indications.

For carrying out an indication as described above, when Expression (10) is not established in the judgment of step 50 of FIG. 4, the respective processes shown in dotted line in the drawing are executed. Concretely, first, the newest total number of the detected light-emitting particle X(tn) computed in step 40 is indicated on the display (step 52). In this connection, when the repetitive executions of steps 30-50 have been already executed, the value of the total number X(tn) of the detected light-emitting particles so far is updated. Subsequently, in order to compute the measurement end time TE or the measurement remaining time Tr, the detection rate v of the light-emitting particle after the start of the processes of step 30-50 is computed (step 54). The detection rate v of the light-emitting particle till the present may be given by:

$$v=X(t_n)/(Tp-Ts) \qquad (11)$$

Here, Tp is the present time. Thus, using the detection rate v of the light-emitting particle, the measurement remaining time Tr (time to the end of the processes of steps 30-50) is estimated as:

$$Tr=(XE-X(t_n))/v \qquad (12)$$

Moreover, the measurement end time TE (time of the end of the processes of steps 30-50) is estimated as:

$$TE=Tp+Tr \qquad (13)$$

(Step 56). Then, the estimated measurement end time TE or the measurement remaining time Tr is indicated on the display (step 58). In this connection, when the repetitive executions of steps 30-50 have been already executed, the already indicated values are updated. Further, when $X(t_n)=0$, it may be indicated that Tr and TE are unknown without calculating Expression (12) or (13).

By the way, as already noted, the above-mentioned processes of steps 30-50 in FIG. 4 and steps 100-170 in FIG. 5 are repeated every analytical time interval t. In this respect, the light intensity measurement of step 100 of FIG. 5 may be continuously performed from the start of measurement to its end even during the execution of the signal processing steps other than step 100. Namely, in the processing cycle of FIGS. 4-5, when the light intensity measurement for the analytical time interval t of one cycle of step 100 is completed, the light intensity measurement of step 100 in the analytical time interval t of the following cycle is performed continuously, and simultaneously, the processes of the detecting and counting of signals of light-emitting particles from the light intensity data acquired in the analytical time interval t of the completed cycle are performed in the computer 18. Thereby, the detecting and counting of light-emitting particles will be achieved in real time.

(3) Analysis, Such as Concentration Computation, Etc.

Thus, when the number of light-emitting particles reaches the end particle count, an analysis, such as a concentration computation, etc., may be performed using the time T (=TE−Ts) until the number of light-emitting particles reaches the end particle count or other information which can be obtained from the detected signal(s) of the light-emitting particle(s) (step 70).

As already noted, for a light-emitting particle concentration, a particle detection rate V is computed with Expression (3) from the time T to reach the end particle count and the end particle count XE, and the light-emitting particle concentration is determined from the particle detection rate V, using the relation of Expression (4).

In this regard, although the cross sectional area S of the passing region of the light detection region in Expression (1)-(4) may be computed theoretically based on the wavelength of excitation light or detected light, the numerical aperture of a lens and the adjustment condition of the optical system, the cross sectional area S may be determined experimentally, for example, from the number of light-emitting particles, detected by performing the light intensity measurement, the detecting and counting of light-emitting particles as explained above for a solution having a known light-emitting particle concentration (a control solution) under the same conditions as the measurement of a sample solution to be tested, and the light-emitting particle concentration of the control solution. Concretely, for example, for a control solution having a light-emitting particle concentration C, supposing the number of detected light-emitting particles in a light intensity measurement performed at the moving speed uo for a certain time τo is N, the cross sectional area S of the passing region of the light detection region is given by:

$$S=N/(C \cdot N_A \cdot uo \cdot \tau o) \quad (14)$$

Furthermore, by preparing the plurality of solutions of different light-emitting particle concentrations as control solutions and performing measurements for the respective solutions, the average of computed Ss may be employed as the cross sectional area S of the light detection region. In this regard, the cross sectional area S of the light detection region may be given by an arbitrary method, for instance, using FCS and FIDA, instead of the above-mentioned method. Further, in the optical analysis device of this embodiment, there may be previously memorized in a storage apparatus of the computer 18 the information on the relations (Expression (14)) between concentrations C and light-emitting particle numbers N of various standard light-emitting particles for assumed moving patterns of the light detection region, so that a user of the device can appropriately use the memorized information on the relation in conducting an optical analysis.

(4) Modified Examples of Processes of Light Intensity Measurement of a Sample Solution and Detecting and Counting of Light-Emitting Particles In the above-mentioned processes of the light intensity measurement of a sample solution, and the detecting and counting of light-emitting particles, as an alternative manner, the analytical time interval t may not be a fixed value but may be modified according to the detecting condition of the light-emitting particles. FIG. 8A shows in the form of a flow chart the processes of the light intensity measurement of a sample solution and the detecting and counting of light-emitting particles, designed so as to include a process (step 20') of modifying the analytical time interval t according to the condition of detecting light-emitting particles, and FIG. 8B shows the process of calculating the analytical time interval t in step 20' in the form of a flow chart. In this regard, in FIG. 8A, the same processes as in FIG. 4 are provided with the same step numbers.

Referring to the drawing, in the processes of FIG. 8, whenever the light intensity measurement for the analytical time interval t is completed, the analytical time interval t is modified (step 20'). Further, especially the processes in the illustrated example are designed to execute the processing cycles of the light intensity measurement and the detecting and counting of light-emitting particles only a predetermined number of times N (referred to as "number of times of scheduled updating" in the following.) in one measurement from its start until the number of light-emitting particles reaches the end particle count XE. Concretely, first, when the processes of the light intensity measurement, the detecting and counting of light-emitting particles are performed in the beginning after the setting of the end particle count XE (step 10) and the memorizing of the start time Ts (step 25) for the initial setting, namely, when the execution times k of the processing cycle of the light intensity measurement and the detecting and counting of light-emitting particles is 0, the initial value to, arbitrarily settable, is given as the analytical time interval t (see FIG. 8B steps 200, 210). And, the execution times k of the processing cycle increases by one (step 270), and the processes of the light intensity measurement and the detecting and counting of light-emitting particles for the analytical time interval t are performed (steps 30-50) similarly to the processes described in FIG. 4. Then, when the number of light-emitting particles x of the first cycle (=X $(t_1)$) is obtained, the particle detection rate v (step 54) and the measurement remaining time Tr (step 56) are computed sequentially. In this connection, similarly to the case of FIG. 4, the total number of the detected light-emitting particles X $(t_n)$ and/or the measurement end time TE or the measurement remaining time Tr are indicated on a display, such as a monitor, etc. of the computer 18 (steps 52 and 58). Also, when the number of light-emitting particles has reached the end particle count XE in the first processing cycle, the processes of the light intensity measurement and the detecting and counting of light-emitting particles are ended (step 50).

After the first processing cycle, the modifying of the analytical time interval t and the processing cycle of the light intensity measurement and the detecting and counting of light-emitting particles, similar to those in FIG. 4, (Steps 20', 30-58) are repeated until the number of light-emitting particles reaches the end particle count XE. In that case, in step 20' of modifying the analytical time interval t, first, it is judged whether or not the number of light-emitting particle X (tn) detected so far is 0 (step 220). If X(tn)=0, the analytical time interval t in the last cycle may be increased in times (m is one or more positive value). If X(tn)>0, using the measurement remaining time Tr, the number of times of scheduled updating N, and the execution time k of the processing cycle, the analytical time interval t is computed by:

$$t = Tr/(N-k) \quad (15)$$

(step 240). In this connection, for the analytical time interval t to be computed, its lower limit may be set, when the analytical time interval t is less than the lower limit tmin, the analytical time interval t may be set as the lower limit tmin (steps 250, 260).

As described above, according to the manner in which the analytical time interval t is modified, the condition of detecting the light-emitting particles to be observation objects in the sample solution is reflected in the measurement remaining time Tr, and therefore, the analytical time interval t will be optimized according to the condition of detecting light-emitting particles.

Thus, according to the above-mentioned present invention, in the scanning molecule counting method to scan the inside of a sample solution with a light detection region and detect light-emitting particles individually, by the manner of repeating the light intensity measurement and the detecting and counting of light-emitting particles until the number of signals from light-emitting particles reaches a predetermined number, the time taken for the light intensity measurement and the detecting and counting of light-emitting particles (the measuring time) will be increased or decreased in accordance with a light-emitting particle concentration in the sample solution. And by setting the predetermined number to be reached by the number of signals from light-emitting particles to the number which provides an accuracy requested in a result, it becomes possible to obtain an allowable or satisfiable result without taking the measuring time longer than needed.

In order to verify the validity of the present invention explained above, the experiments described below were conducted. In this regard, it should be understood that the following embodiments illustrate the validity of the present invention only, not intended to limit the scope of the present invention.

Embodiment 1

Detecting and counting of light-emitting particles were performed by the scanning molecule counting method with a solution in which fluorescent dye molecules were dissolved as a sample solution, and together with checking the feature of the scattering of the number of light-emitting particles, it was verified that, in accordance with the present invention, a light-emitting particle concentration was precisely detectable as short a time as possible with suppressing the scattering of the result irrespective of the light-emitting particle concentrations.

As sample solutions, there were prepared solutions in which ATTO633(sigma Aldrich (Sigma-Aldrich), Cat. No. 18620) was dissolved so as to be at a concentration of 100 pM, 10 pM, 1 pM and 100 fM in a PBS buffer solution containing 0.05% Tween 20, respectively. In the light measurement, a single molecule fluorescence measuring apparatus MF-20 (Olympus Corporation), equipped with the optical system of a confocal fluorescence microscope and a photon counting system, was used as the optical analysis device, and time series light intensity data (photon count data) were acquired for the above-mentioned respective sample solutions in accordance with the manner explained in the above-mentioned "(2) (ii)(a) Light Intensity Measurement of a Sample Solution". In that time, a 633-nm laser light was used for excitation light, and, using a band pass filter, the light of the wavelength bands, 660 to 710 nm, was measured, and time series light intensity data was generated. The position of the light detection region in the sample solution was moved at the moving speed of 30 mm/second. Further, BIN TIME was set to 10 μseconds and measurements were performed 5 times for the respective solutions. In this connection, since this experiment was for checking the feature of the scattering in the number of light-emitting particles, the light intensity measurement was not performed every analytical time interval, but was performed for a sufficient time to be able to catch the feature of the scattering in the number of light-emitting particles (In actual, the measuring time was set to 2 seconds for the solutions of 100 pM, 10 pM and 1 pM and to 20 seconds for the solution of 100 fM.).

After the light intensity measurement, in accordance with the procedures described in the above-mentioned "(2)(ii)(b) Detection of a signal corresponding to a light-emitting particle", the smoothing treatment was applied to the time series light intensity data acquired above and after determining the start points and the end points of pulse signals in the smoothed data, the fitting of a Gauss function to each pulse signal was carried out by the least square method, and a peak intensity, a pulse width (full width at half maximum) and a correlation coefficient (in the Gauss function) were determined. And, only the pulse signal satisfying the following conditions:

20 μsec.<pulse width<400 μsec.

Peak intensity>1.0 [pc/10 μsec.] (A)

Correlation coefficient>0.95 was judged as a signal corresponding to a light-emitting particle, while a pulse signal which did not satisfy the above-mentioned conditions was disregarded as noise.

FIG. 9A shows variations of the scatterings in the number of the detected light-emitting particles against the measuring time length in the scanning molecule counting method. In the drawing, the abscissa indicates the measuring time length and the ordinate indicates CV values (=standard deviation/average×100%) of the number of light-emitting particles detected in the five measurements, wherein each point shows the CV value in the corresponding measuring time length. As understood from the drawing, in all of the above-mentioned sample solutions of 10 pM, 1 pM and 100 fM, the CV value was reduced as the measuring time became longer. Also, as seen clearly in comparison of the values of the three sample solutions, it was confirmed that it took much time to make the CV value sufficiently smaller as the concentration became lower. Accordingly, it was shown that the measuring time taken for the scattering of the number of detected light-emitting particles to fall within an allowable range differs depending upon the light-emitting particle concentrations in sample solutions.

On the other hand, FIG. 9B shows variations of the scatterings of the measuring time (particle detection time) taken to acquire the respective numbers of detected light-emitting particles against the corresponding detected numbers. In the drawing, the abscissa indicates the number of detected light-emitting particles, wherein each point shows the CV value (=standard deviation/average×100%) of the measuring time (particle detection time) taken to detect the corresponding number of the light-emitting particles in the five measurements. As understood from the drawing, in the above-mentioned three sample solutions, when the number of light-emitting particles exceeded beyond 30, the dependency of the CV value of the particle detection time on the light-emitting particle concentration was almost lost. This suggests that, in the scanning molecule counting method, a result having small scattering can be obtained by conducting the light intensity measurement until the number of the signals from the light-emitting particles reaches the number providing an accuracy requested in a result, and carrying out an analysis of the concentration, etc. based on the measuring time taken to acquire the number of the detected light-emitting particles therein.

Moreover, with reference to the result of FIG. 9B, in the light intensity data obtained for the solutions of the dye molecule concentration at 100 fM and at 10 pM, the measuring times and the particle detecting rates until the number of the detected light-emitting particles reached 130 were compared with one another. The results were as follows:

TABLE 1

10 pM ATTO633

| | Measuring Time (sec.) | Particle Detection Rate (number/sec.) | Total Detected Number Measuring Time = 2 sec. |
|---|---|---|---|
| 1st | 0.19 | 776.4 | 1382 |
| 2nd | 0.18 | 843.1 | 1532 |
| 3rd | 0.18 | 832.4 | 1432 |
| 4th | 0.17 | 875.4 | 1361 |
| 5th | 0.20 | 730.6 | 1541 |
| Average | 0.18 | 811.6 | 1450 |
| | | SD 57.7, | SD 83.48 |
| | | CV 7.1% | CV 5.8% |

TABLE 2

100 fM ATTO633

| | Measuring Time (sec.) | Particle Detection Rate (number/sec.) | Total Detected Number Measuring Time = 2 sec. |
|---|---|---|---|
| 1st | 13.3 | 11.3 | 220 |
| 2nd | 14.4 | 10.4 | 182 |
| 3rd | 17.0 | 8.82 | 167 |
| 4th | 12.0 | 12.5 | 214 |
| 5th | 14.6 | 10.2 | 169 |
| Average | 14.3 | 10.7 | 190 |
| | | SD 1.38, | SD 25.0, |
| | | CV 12.9% | CV 13.2% |

As understood from the above-mentioned tables, it was shown that, for making the scattering of results fall into an allowable level, the measuring time should be 14 seconds or more in the case of the solution of 100fM, while the measuring time could be about 0.18 second in the case of the solution of 10 pM. This shows that, in the scanning molecule counting method, the measuring time necessary for obtaining a result at a sufficient accuracy with suppressing the scattering small differs depending upon light-emitting particle concentrations. Further, it has been shown that, according to the manner of the present invention of performing the light intensity measurement until the number of detected light-emitting particle becomes a predetermined number, the light intensity measurement will be performed in the measuring time in accordance with a light-emitting particle concentration and it can be avoided to spend time for the measurement more than needed. It should be understood that, especially for a high light-emitting particle concentration, the measuring time can be shortened substantially.

Furthermore, FIG. 10 shows a drawing in which the particle detecting rates, computed from the measuring time to 150 of the detected number in the above-mentioned respective sample solutions, are plotted against the corresponding concentrations. As understood from the drawing, the particle detection rate is proportional to the dye concentration, suggesting that the relation of the above-mentioned Expression (4) is established. Thus, it has been shown that a light-emitting particle concentration in a sample solution can be determined based on the particle detecting rate or the measuring time taken to detect a predetermined number of light-emitting particles.

Thus, as understood from the results of the above-mentioned embodiments, according to the above-mentioned present invention, in the scanning molecule counting method, by the manner of performing the light intensity measurement with moving a light detection region and the detection of a light-emitting particle, not for a certain fixed measuring time, but until the number of signals from light-emitting particles reaches a predetermined number, it becomes possible to optimize the measuring time with suppressing the scattering in a result small, and to complete the measurement for the detection of the number of light-emitting particles achieving an accuracy requested in a result as short a time as possible. Especially, since, in the present invention, the signal of a light-emitting particle is detected individually, the detection of a light-emitting particle is possible even when a light-emitting particle concentration in a sample solution is lower than the concentration range demanded by optical analysis techniques, such as FCS, and this feature is will be advantageous in conducting an analysis of a rare or expensive sample often used in the field of medical or biological research and development. Moreover, in accordance with the present invention, even when a light-emitting particle concentration in a sample solution is unknown, the labor, time or expense in the trial and error for the measuring time can be reduced, and therefore, the expansion of the application area of the scanning molecule counting method is expected. For instance, it becomes unnecessary to set a long measuring time for a case of an extremely low light-emitting particle concentration because of the light-emitting particle concentration in a sample solution being unknown.

The invention claimed is:

1. A method of detecting and analyzing light from a light-emitting particle dispersed and moving at random in a sample solution using an optical system of a confocal microscope or a multiphoton microscope, comprising:
repeating steps (a), (b), (c), (d) and (e):
(a) moving a position of a light detection region of the optical system in the sample solution by changing an optical path of the optical system,
(b) detecting light from the light detection region while moving the position of the light detection region in the sample solution, over a plurality of units of time,
(c) generating a time series light intensity data of the light from the light detection region detected while moving the position of the light detection region in the sample solution, (d) smoothing data values of the light detected over the plurality of units of time, said smoothing being conducted until a gap in a light intensity variation over the plurality of units of time of a light signal from a light-emitting particle can be disregarded, and (e) detecting the particle individually based on smoothed data values by detecting, as a light signal of the particle, a light intensity variation over consecutive units among the plurality of units of time which has a predetermined profile which is expected from a single light-emitting particle moving relatively inside the light detection region, while disregarding a light intensity variation over consecutive units among the plurality of units of time which does not have the predetermined profile as noise, until the number of signals from the light-emitting particles detected by the step (e) reaches a predetermined number; and determining a concentration of the light-emitting particles in the sample solution based on a time taken for the number of the signals from the light-emitting particles to reach the predetermined number, wherein the light detection region of the optical system in the sample solution is moved at a speed greater than the speed of movement of the light-emitting particle due to Brownian motion.

2. The method of claim 1, wherein the steps (a), (b), (c), (d) and (e) are repeated every predetermined interval in a period until the number of the signals from the light-emitting particles reaches the predetermined number.

3. The method of claim 1, wherein the concentration of the light-emitting particles in the sample solution is determined based on the detection rate of the light-emitting particles determined based on the time taken for the number of the signals from the light-emitting particles to reach the predetermined number.

4. The method of claim 1, further comprising a step of estimating the time taken for the number of the signals from the light-emitting particles to reach the predetermined number based on the number of the detected light-emitting particles so far in the period until the number of the signals from the light-emitting particles reaches the predetermined number.

5. The method of claim 1,
wherein the steps (a), (b), (c), (d) and (e) are repeated every predetermined interval in the period until the number of the signals from the light-emitting particles reaches the predetermined number, and
wherein the method further comprises a step of modifying the predetermined interval based on the number of the light-emitting particles detected so far.

6. The method of claim 1, wherein the position of the light detection region is moved at a velocity quicker than a diffusional moving velocity of the light-emitting particle in the light detection region moving step.

7. The method of claim 1, wherein the predetermined profile which is expected from a single light-emitting particle moving relatively inside the light detection region has an approximately bell shape.

8. The method of claim 1,
wherein, after step (d), a pulse existing region is determined by referring to the time differential value sequentially, and
wherein after the pulse existing region is determined, an individual particle is detected by fitting the predetermined profile to the smoothed data values in the pulse existing region, in step (e).

* * * * *